US007708985B2

(12) United States Patent
Morre et al.

(10) Patent No.: US 7,708,985 B2
(45) Date of Patent: May 4, 2010

(54) GLYCOSYLATED IL-7, PREPARATION AND USES

(75) Inventors: Michel Morre, Boulogne (FR); Brigitte Assouline, Courbevoie (FR); Iann Rance, Sevres (FR); Anne Gregoire, Auzecort (FR); Corinne Breque, Vanves (FR)

(73) Assignee: CYTHERIS, Issy les Moulineaux (FR)

( * ) Notice: Subject to any disclaimer, the term of this patent is extended or adjusted under 35 U.S.C. 154(b) by 0 days.

(21) Appl. No.: 11/996,176

(22) PCT Filed: Jul. 19, 2006

(86) PCT No.: PCT/IB2006/002663

§ 371 (c)(1),
(2), (4) Date: Jan. 18, 2008

(87) PCT Pub. No.: WO2007/010401

PCT Pub. Date: Jan. 25, 2007

(65) Prior Publication Data

US 2008/0206190 A1    Aug. 28, 2008

(30) Foreign Application Priority Data

Jul. 20, 2005    (EP)    .................................. 05291556

(51) Int. Cl.
*A61K 38/20*    (2006.01)
*C12N 5/06*    (2006.01)

(52) U.S. Cl. ...................... 424/85.2; 435/325

(58) Field of Classification Search ........................ None
See application file for complete search history.

(56) References Cited

U.S. PATENT DOCUMENTS

| 5,153,310 A | 10/1992 | Mitchell et al. |
| 5,328,988 A | 7/1994 | Namen et al. |
| 2005/0249701 A1 | 11/2005 | Morre et al. |

FOREIGN PATENT DOCUMENTS

EP    1391513 A1    2/2004

OTHER PUBLICATIONS

University of Michigan museum of Zoology web page: http://animaldiversity.ummz.umich.edu/site/accounts/information/Canidae.html; accessed Apr. 22, 2009.*
Wells, Additivity of Mutational Effects in Proteins, Biochemistry, 29:8509-8517, 1990.*
Skolnick et al., From genes to protein structure and function:novel applications of computationalapproaches in the genomic era.Trends in Biotech. 18(1):34-39,2000.*
Ju et al., Conversion of the interleukin 1 receptor antagonist into an agonist by site-specific mutagenesis. Proc. Natl. Acad. Sci. USA, 88, 2658-2662, 1991.*
Whisstock et al, Prediction of protein function from protein sequence and structure. Quarterly Rev. Biophys. 36, 307-340, 2003.*
Whistow et al., Tau-Crystallin/alpha-Enolase: One Gene Encodes Both an Enzyme and a Lens Structural Protein, J. Cell Biol.107, 2729-2736, 1988.*
Axford, J.S. et al. "Glycobiology and Medicine" *CPD Bulletin. Immunology and Allergy* 2004, pp. 85-88, vol. 3, No. 3.
Cebo, C. et al, "Lectin activities of cytokines: functions and putative carbohydrate-recognition domains" *Biochemica et Biophysica Acta*, Sep. 19, 2002, pp. 422-434, vol. 1572, No. 2-3.
Goodwin, R.G. et al. "Human interleukin 7: molecular cloning and growth factor activity on human and murine B-lineage cells" *PNAS*, Jan. 1989, pp. 302-306, vol. 86.
Database Geneseq [Online], Nov. 4, 2004, XP002366778, Database Accession No. ADR05996, pp. 1-2.

\* cited by examiner

*Primary Examiner*—Christine J Saoud
*Assistant Examiner*—Elly-Gerald Stoica
(74) *Attorney, Agent, or Firm*—Saliwanchik Lloyd & Saliwanchik

(57) ABSTRACT

The present invention relates to new and improved interleukin-7 polypeptides, as well as compositions comprising the same, their preparation and uses. The invention more particularly relates to hyperglycosylated IL-7 polypeptides having improved properties, as well as their manufacture and therapeutic uses. The invention also discloses novel IL-7 polypeptides having modified amino acid sequences containing artificially created glycosylation site(s), as well as corresponding nucleic acid molecules, vectors and recombinant host cells. The invention also relates to the use of such polypeptides, cells or nucleic acids for curative or preventive treatment of mammalian subjects, including human subjects.

13 Claims, 10 Drawing Sheets

US 7,708,985 B2

GLYCOSYLATED IL-7, PREPARATION AND USES

CROSS-REFERENCE TO RELATED APPLICATION

Figure 1:
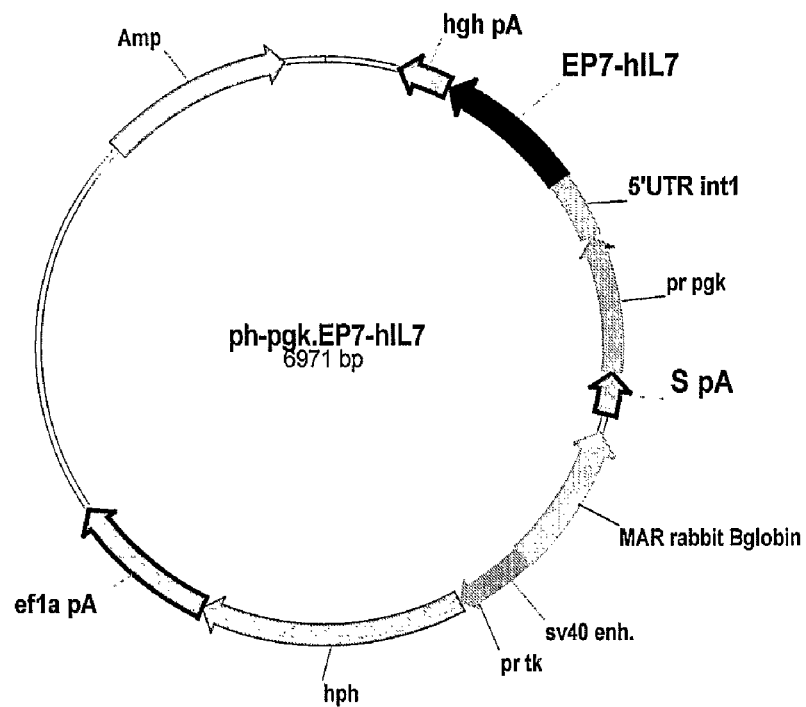

This application is the U.S. national stage application of International Patent Application No. PCT/IB2006/002663, filed Jul. 19, 2006, the disclosure of which is hereby incorporated by reference in its entirely, including all figures, tables and amino acid or nucleic acid sequences.

The present invention relates to new and improved interleukin-7 polypeptides, as well as to compositions comprising the same, their preparation and uses. The invention more particularly relates to hyperglycosylated IL-7 polypeptides having improved properties, as well as their manufacture and therapeutic uses. The invention also discloses novel IL-7 polypeptides having modified amino acid sequences containing artificially created glycosylation site(s), as well as corresponding nucleic acid molecules, vectors and recombinant host or host cells. The invention also relates to the use of such polypeptides, cells or nucleic acids for curative or preventive treatment of mammalian subjects, including human subjects.

BACKGROUND OF THE INVENTION

B and T lymphocytes are the primary effector cells of the immune responses. Both cell classes are considered to derive ultimately from hematopoietic stem cells in the mammalian bone marrow, via progenitor or precursor cells representing distinguishable stages in the differentiation of each class. Mature T cells develop principally in the thymus, presumably from a precursor cell which migrates from the bone marrow to the thymus at an early stage of T lymphocyte development. Lymphoid cells development is dependent on growth, survival and differentiation factors produced by various stromal cells. Numbers of factors are active on mature peripheral B and T cells, including IL-1, IL-2, IL-4, IL-5, interferon gamma, BSF-2, neuroleukin, transforming growth factor beta and IL-7.

"Interleukin-7" or "IL-7" refers to a mammalian endogenous secretory glycoprotein which is capable of inducing proliferation of bone marrow-derived lymphocyte progenitors and precursors, including the specialized precursors known as pre-B cells. Originally derived from the stromal element of a bone marrow cell line, IL-7 is also secreted by thymic stromal cell, intestinal and other epithelial cells, some dendritic cells and follicular dendritic cells, keratinocytes and generally all lymphoid tissues. Alternative designations for this molecule are "pre-B cell growth factor" and "lymphopoietin-1".

EP0314415 (or U.S. Pat. No. 4,965,195) describes mammalian interleukin-7 proteins and corresponding DNAs. Human IL-7 amino acid sequence contains three putative N-linked glycosylation sites, located at Asn residues at positions 70, 91 and 116. Transient recombinant expression of hIL-7 (human IL-7) in COS cells allowed the visualization of r-huIL-7 (recombinant human IL-7) as three protein bands of apparent molecular weight of about 20, 24 and 28 kDa (Cosman et al.; Lymphokine Receptor Interactions; 1989; 179: 229-236). Stable recombinant expression of hIL-7 in BHK cells was also reported (Armitage et al.; The Journal of Immunology; 1990; 144:938-941). However, the glycosylation status of naturally-occurring human IL-7, particularly the O-glycosylation status, has never been documented or studied, and the impact of the glycosylation profile on IL-7 properties has never been considered. Furthermore, unglycosylated mature human IL-7 (r-hIL-7) produced in *E. coli*, as described in EP0314415, exhibits a 17,387 Daltons molecular weight and displays a high activity in vitro on specific bioassays based on the proliferation of various lymphocytes populations. Other cytokines and growth factors, such as G-CSF, GM-CSF, IFN, HGF, etc, also display full therapeutic activity without glycosylation.

WO2004/018681 discloses an active conformer of human IL-7, comprising the following disulfide bridges: 1-4 (C2-C92), 2-5 (C34-C129) and 3-6 (C47-C141), as well as methods of producing or characterizing the same and the uses thereof.

IL-7 was originally disclosed as a cytokine whose principal activity was the induction of precursor B cell proliferation (Namen A. E. et al.; Journal of Experimental medicine; 1988; 167:988-1002). IL-7 has more recently been disclosed as being involved in the survival and proliferation of thymocytes (T-Cells) during early stage of T-cell development (Schluns K. S. et al.; Nature Immunology; 2000; 1(5):426-432). IL-7 pathway is essential for lymphocyte development notably on developing thymocytes (Maeurer M. J. et al.; Int. Rev. Immunol.; 1998; 16:309-22-Fry T. J. et al.; Blood; 2002; 99:3892-904). Fry and collaborators further identified IL-7 as a potent modulator of thymic-independent T-cell regeneration in a multifactorial action (Fry T. J. et al.; Blood; 2001; 97(6):1525-1533). IL-7 potently modulates mature T cells and beside this effect on mature T cells, IL-7 may influence the development of antigen presenting cells (Marquez C. et al.; J. Exp. Med.; 1995; 181:475-83). IL-7 is essential for memory T cell regeneration, both in the CD4+ and CD8+ subsets (Kondrack R. M. et al.; J. Exp. Med.; 2003; 198:1797-806-Kaech S. M. et al.; Nat. Immunol.; 2003; 4:1191-8).

IL-7 has thus a great therapeutic potential for use in the stimulation of the proliferation of T cell precursors, of antibody-secreting B cells, in the stimulation of antigen driven T-cell peripheral expansion, and in the production of naïve T-cells as well as other hematopoietic cell types. A particularly interesting therapeutic use of active IL-7 molecules is for immune reconstitution of lymphopenic patients: patients treated for a cancer, patients having received a bone marrow or a stem cell transfer, patients presenting an acquired or genetic immune deficiency, elderly patients or any patients having low CD4 count. Other utilities reside in the ability of IL-7 to produce new naïve CD4 T-cells or to expand specific pools in order to produce or increase specific immune responses (vaccine enhancement).

In view of its therapeutic potentials, there is considerable interest in developing biologically active or improved IL-7 polypeptides that are suitable for efficient therapeutic uses. In this respect, among the various cytokines and growth factors commercially available, some are poorly immunogenic (e.g., Interferon alfa "IFNα", granulocyte colony stimulating factor "G-CSF") so that the corresponding drug substances do not require a very specific polypeptide purity other than conventional level usually accepted for recombinant proteins. In contrast, other growth factors are more immunogenic (e.g., Beta interferon "β-IFN", Granulocyte Macrophage Colony stimulating factor "GM-CSF") or their specific activity is so critical for life (e.g., Erythropoietin "EPO") that drug substance polypeptide purity and profile must be specifically studied and maintained inside narrow limits to preserve from immunogenicity.

IL-7 is a unique molecule. Due to its intrinsic immune-enhancing properties, IL-7 used as a therapeutic agent is particularly prone to trigger anti-IL-7 immunogenicity (anti-IL-7 binding or neutralizing antibodies). This immunogenicity is deleterious for the long term therapeutic activity of the protein. Anti-IL-7 antibodies can modify IL-7 pharmacokinetic and neutralize its therapeutic activity.

Various IL-7 isoforms are involved in triggering anti-IL-7 immunogenicity, among which: altered polypeptide sequences (e.g., oxidized, reduced, deamidated or truncated forms), covalent or non covalent IL-7 multimers, such as aggregated IL-7 molecules and the like. Therefore it is critical to define IL-7 polypeptides and drug substances which are more stable, less prone to intermolecular aggregation, less immunogenic and still biologically active. Indeed, while the activity of most drugs is correlated with AUC parameter, the activity of IL-7 is correlated to half-life parameter and more particularly to mean residence time.

SUMMARY OF THE INVENTION

The present invention discloses new and improved IL-7 polypeptides, drug substances and compositions. More particularly, the invention discloses novel IL-7 molecular species having a high degree of glycosylation and an oligosaccharide profile shifted to a higher molecular size with increased sialylation and fucosylation of the carbohydrate moieties and a lower isoelectric point. The invention shows that these new oligosaccharide profiles confer improved chemical and pharmaceutical stability to these new drug substances and a prolonged pharmacokinetic profile after in vivo administration, characterized by an increased mean residence time (MRT), allowing a less frequent dosing schedule.

The present invention therefore provides novel highly glycosylated or hyperglycosylated IL-7 polypeptides having improved properties. The invention also discloses novel IL-7 polypeptides having modified amino acid sequences containing artificially created glycosylation site(s), as well as corresponding nucleic acid molecules, vectors and recombinant host or host cells. The invention also relates to the use of such polypeptides, cells or nucleic acids for curative or preventive treatment of mammalian subjects, including human subjects. The present invention thus discloses novel active IL-7 polypeptides, drug substances and pharmaceutical compositions, which exhibit increased stability, reduced susceptibility to proteolysis and aggregation, advantageous in vivo long term activity and reduced immunogenicity, thereby allowing improved global or specific immune responses to be generated in mammalian subjects.

An object of this invention resides in a hyperglycosylated IL-7 composition.

A further object of this invention resides in a purified hyperglycosylated IL-7 polypeptide.

Such hyperglycosylated IL-7 polypeptide contains at least three N-glycosylated amino acid residues.

A further object of this invention relates to the use of hyperglycosylated IL-7 for the manufacture of a medicament consisting of said hyperglycosylated IL-7 and a pharmaceutically acceptable excipient or vehicle, for treating a mammalian subject.

A further object of this invention relates to the use of a hyperglycosylated IL-7 composition for the manufacture of a medicament for treating a mammalian subject.

A further object of this invention is a method of causing or stimulating an immune response in a subject, comprising administering to the subject an effective amount of a hyperglycosylated IL-7 composition.

A further object of this invention is a method for ex-vivo enhancing expansion of T cells, which method comprises contacting T cells with a hyperglycosylated IL-7 polypeptide or composition, hereby enhancing expansion of the T cells.

In a particular embodiment, the hyperglycosylated IL-7 composition is a composition comprising at least 80%, preferably between 80% and 95%, IL-7 polypeptides which are glycosylated on at least three distinct amino acid residues. Such residues may be either naturally present within an IL-7 polypeptide sequence and/or artificially created glycosylation sites(s).

In a further particular embodiment, the hyperglycosylated IL-7 composition is a composition comprising at least 80%, preferably between 80% and 95%, IL-7 polypeptides which are glycosylated on from three up to eight distinct amino acid residues, including one O— and up to seven N-glycosylation sites. Such residues may be either naturally present within an IL-7 polypeptide sequence and/or artificially created N-glycosylation sites(s).

In this regard, a further object of this invention relates to IL-7 polypeptides having a modified amino acid sequence, wherein said sequence comprises at least one artificially created glycosylation site. According to particular embodiments, the IL-7 polypeptides of this invention comprise 1, 2, 3 or 4 artificially created glycosylation sites, more preferably 1, 2 or 3; even more preferably 1 or 2. As will be disclosed further, the artificially created glycosylation sites are preferably N-linked glycosylation sites. The IL-7 polypeptides of this invention may be from any mammalian origin, particularly of human origin. Furthermore, such IL-7 polypeptides may comprise the sequence of a mature IL-7 polypeptide, or further comprise additional amino acid residues, such as a secretion peptide for instance. In addition, or in the alternative, the IL-7 polypeptide is preferably a specific conformer comprising the following three disulfide bridges: Cys: 1-4 (Cys2-Cys92); 2-5 (Cys34-Cys129); 3-6 (Cys47-Cys141). Specific examples of such modified IL-7 polypeptides comprise at least one amino acid modification as disclosed in Table 1 below, or a combination thereof.

A further object of this invention resides in a nucleic acid molecule encoding an IL-7 polypeptide as discussed above. The nucleic acid molecule may be any DNA or RNA molecule, typically a cDNA molecule.

A further object of this invention resides in a nucleic acid molecule encoding secretion signal comprising SEQ ID NO: 19.

A further object of this invention resides in a vector comprising a nucleic acid molecule as defined above. The vector may be any prokaryotic or eukaryotic vector, typically a eukaryotic vector, and may be selected from a plasmid, episomal DNA, cosmid, viral vector, artificial chromosome, etc. The vector may comprise any regulatory sequence allowing proper expression of the coding nucleic acid in a selected host cell, e.g., a promoter, terminator, polyA, origin of replication, homologous region, intron, genes 5' or 3' untranslated regions (UTR) etc.

The above nucleic acids and vectors may be used for instance to produce recombinant mammalian IL-7 polypeptides in various competent host cells, as well as for gene therapy purposes.

Another object of this invention resides in a recombinant host cell comprising a nucleic acid or a vector as disclosed above. Such a recombinant cell may be prokaryotic or, more preferably, eukaryotic, such as a yeast, insect, plant or mammalian cell, for instance, more preferably, recombinant host cell transduced to express or over express a glycosyltransferase and/or a 2-6-sialyltransferase gene, e.g., from human origin.

Another object of this invention resides in a drug substance comprising an IL-7 polypeptide as described above, typically a hyperglycosylated IL-7 polypeptide. More preferably, the drug substance contains less than about 10% of un- or monoglycosylated IL-7 polypeptide and/or is essentially devoid of product-related impurities.

The invention also relates to the use of a drug substance as described above in the manufacture of a medicament ("drug product") or pharmaceutical composition.

The invention further relates to a pharmaceutical composition comprising an effective amount of an IL-7 polypeptide or composition or drug substance as described above and one or more pharmaceutically compatible carriers or excipients.

The invention also provides an antibody, as well as fragments or derivatives thereof, specifically immunoreactive with an IL-7 polypeptide as defined above; hybridoma cell lines that produce said antibody, as well as compositions suitable for diagnosis, assay or therapy comprising said antibody, fragments or derivatives thereof.

A further aspect of this invention is a method of producing an IL-7 polypeptide as described above, from prokaryotic or eukaryotic host cells, as well as a method of detecting or measuring the presence of such an IL-7 polypeptide in a sample, or to characterize a sample.

In a particular aspect, the method of producing an IL-7 polypeptide as defined above comprises:
a) culturing a recombinant host cell as defined above, and
b) collecting the IL-7 polypeptide produced from said cell.

According to a preferred embodiment, expression is performed under conditions allowing efficient glycosylation motifs to be added to the IL-7 polypeptide, in particular sialic acid residues.

In a further preferred embodiment, the production is performed in a fed-batch or perfusion mode maintaining the cells at the end of exponential growth phase. Such conditions increase the quality of post-translational modifications and contribute to a higher degree of sialylation per IL-7 polypeptides. According to particular embodiments, the encoding nucleic acid comprises a secretion signal and/or an optimized nucleic acid sequence and/or the host cell is a eukaryotic host cell (e.g., a mammalian or insects or yeast cell).

Another object of the invention relates to the use of an IL-7 polypeptide or a hyperglycosylated IL-7 composition, as defined above or obtained by a method as described above, for the manufacture of a pharmaceutical composition to cause or modulate an immune response in a subject, particularly to induce prolonged lymphopoiesis stimulation and/or to amplify an immune response.

The invention also relates to the use of an IL-7 polypeptide as defined above or obtained by a method as described above, for the manufacture of a pharmaceutical composition to prevent or treat a disease associated with an immunodeficiency.

As will be discussed below, the polypeptides of this invention exhibit an extended plasma half-life and mean residence time, which favor in vivo receptor interaction and activity, and/or an improved stability and/or a lesser long term immunogenicity, thereby allowing their uses to treat a variety of pathological conditions in mammalian subjects, particularly in human subjects.

LEGENDS TO THE FIGURES

FIG. 1: Plasmid ph-pgk.EP7-hIL-7:
ef1a pA: "elongation factor 1 alpha" poly A sequence; hgh pA: "human growth hormone" poly A sequence; SpA: synthetic polyA sequence; hph: hygromycin resistance; Amp: Ampicillin resistance; MAR rabbit βglobin: putative rabbit βglobin "Matrix Attachment Region"; pr. tk: thymidine kinase promoter, sv40 enh.: sv40 enhancer; pr pgk: phosphoglycerate kinase promoter; 5'UTRint1: 5' untranslated region comprising a chimeric intron (hBglobin-immunoglobuline); EP7-hIL7: optimized human IL-7 cDNA upstream from EP7 signal peptide.

Figure 2:
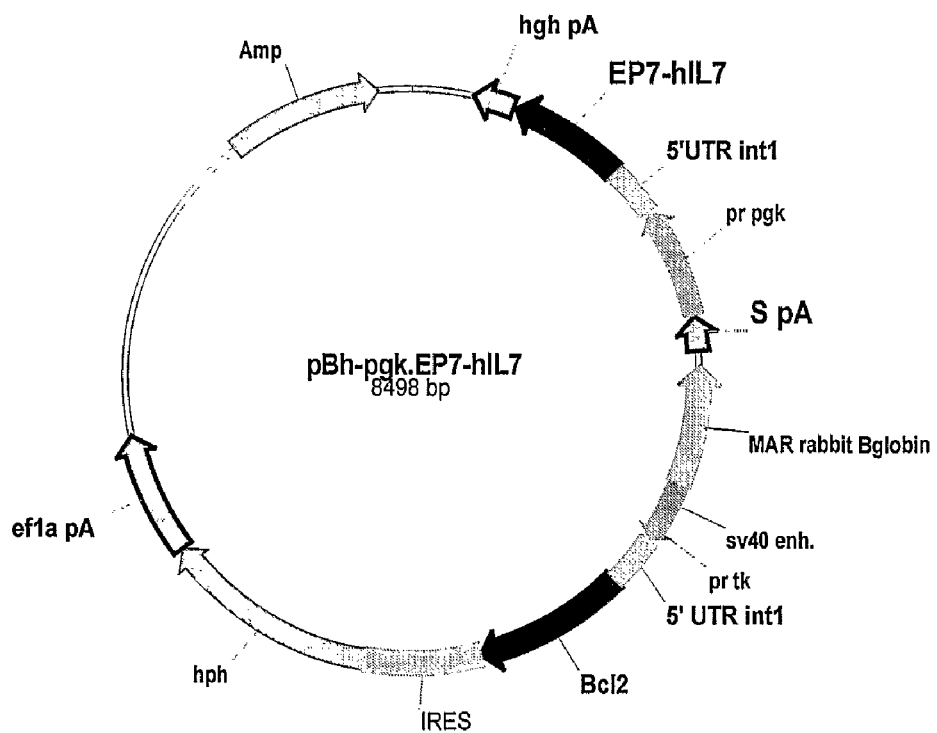

FIG. 2: Plasmid pBh-pgk.EP7-hIL-7:
Bcl2: Bcl2 cDNA; IRES: Internal Ribosome Entry Site FIG. 3: Expression of recombinant hIL-7 in mammalian cells cultured in Bioreactor from day 1 (D1) to day 10 (D10) Westen blot of intracellular versus secreted IL-7.

Figure 4:
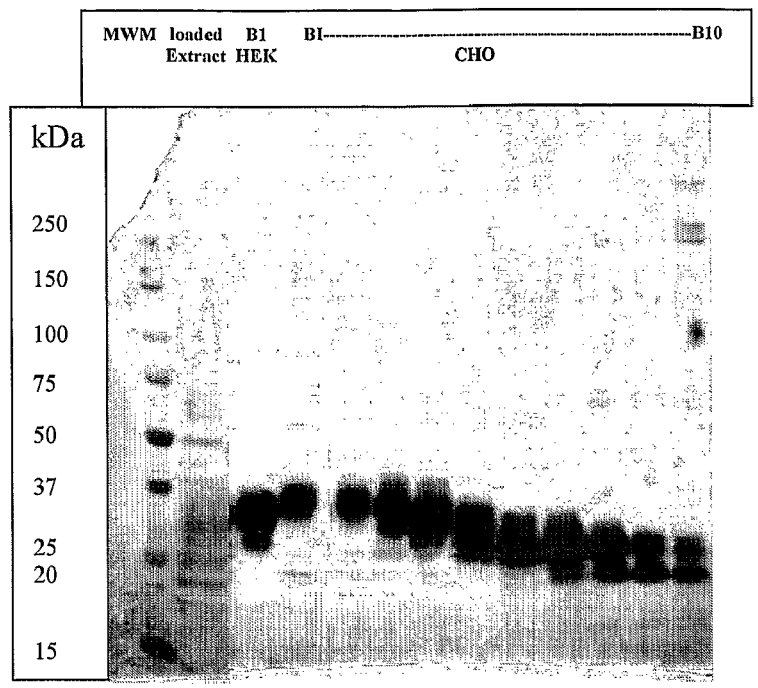

FIG. 4: Chromatographic fractionation of rec-hIL-7glycoforms throughout purification process: SDS PAGE analysis of the protein content in the different elution fractions (B1-B10). IL-7 glycoforms were separated during both the capture and HIC steps. Buffer gradients were used so as to elute differentially the hIL-7 glycoforms according to their slightly different physico-chemical properties. Fractionation and subsequent selection of adequate fraction allowed an enrichment of the fully three glycosylated recombinant hIL-7 (3 N— or 2 N— associated with 1O-sugar moiety). MWM, protein molecular weight markers (10; 15; 20; 25; 37; 50; 75; 100; 150; 250 kDa); B1-B10, elution fractions; B1-B4, elution fractions retained for further purification; CT, fraction B1 obtained from a culture of HEK293 cell line transfected with the same optimized hIL-7 cDNA.

Figure 5:
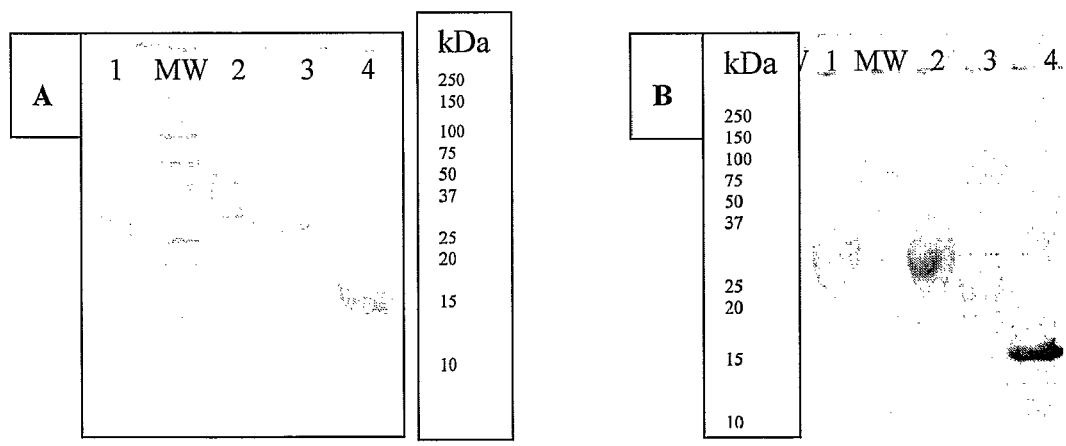

FIG. 5: Analyses of the purified recombinant hIL-7 on SDS PAGE. Samples of the purified recombinant hIL-7 were loaded on SDS PAGE under reducing conditions. Gels were revealed by:
A. Coomassie staining
B. Western blot MWM: molecular weight markers (10; 15; 20; 25; 37; 50; 75; 100; 150; 250 kDa). Lane 1: HG-37-147; Lane 2: HG-40-104; Lane 3: HG-hIL-7; Lane 4: *E. coli* hIL-7.

Figure 6:
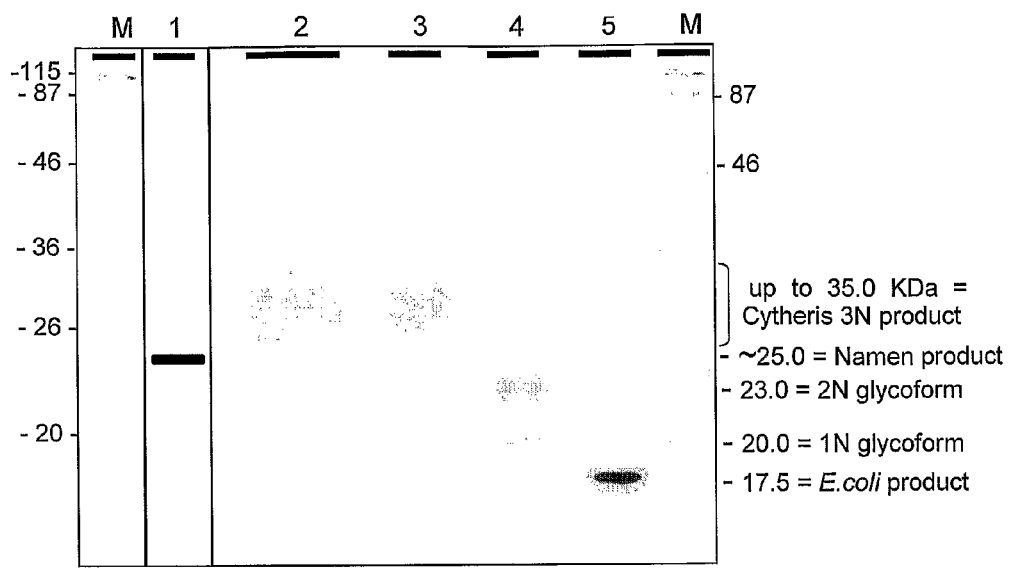

FIG. 6: Comparative SDS-PAGE apparent molecular weight of purified glycosylated rec-hIL-7 products.

Lane M=Molecular weight marker, Lane 1=schematic representation of purified product as described by Namen et al. in patent # U.S. Pat. No. 5,328,988 (about 25 KDa), Lane 2=CHO rec-sIL-7 product purified by the Applicant, Lane 3=CHO rec-hIL-7 product purified by the Applicant, Lane 4=hIL-7 1N- and 2N-glycoforms as standard for apparent molecular weight comparison, Lane 5=*E. coli* rec-hIL-7 product purified by the Applicant (CYT 99 007).

Figure 7:
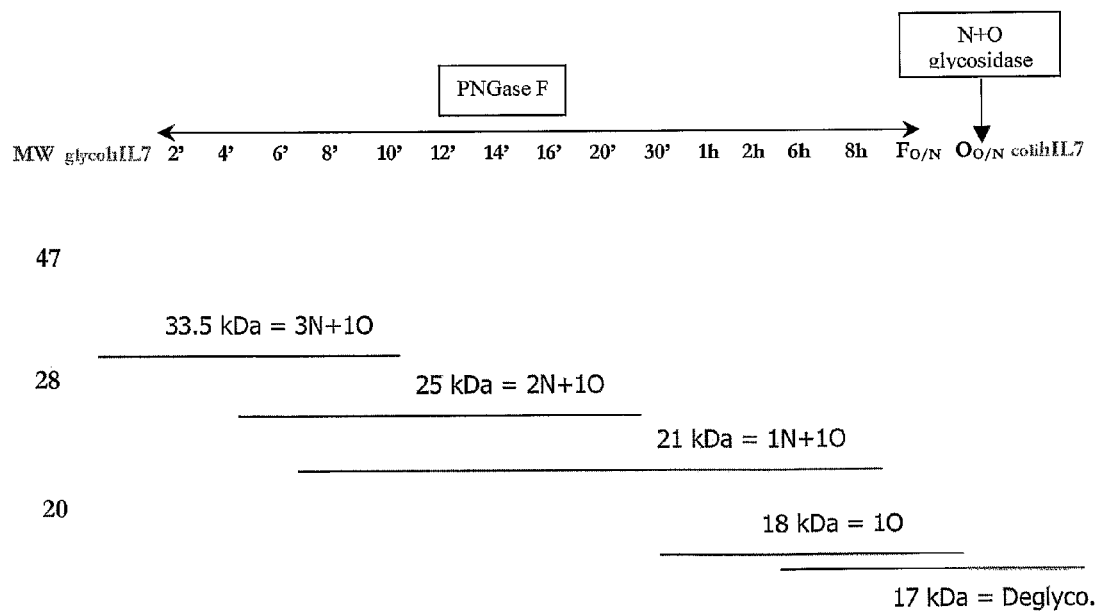

FIG. 7: Analyses of the purified recombinant human IL-7 on SDS PAGE under reducing conditions after deglycosylation.

Samples of the purified recombinant glycosylated human IL-7 were digested by PNGase F: Kinetic samples from 2 minutes to 24 h were loaded on gel.

Another sample (OO/N) was digested over 24 h with PNGase F+O-glycosidase/β(1-4)galactosidase/neuraminidase/N-Acetylglucosaminidase.

As a control, glycosylated human IL-7 and *E. coli* human IL7 were also loaded on the gel.

3N+1O, 2N+1O, 1N+1O, 1O glycoforms and deglycosylated human IL7 were then separated according to their MW estimated on the gel at 33, 27, 24, 18 and 17 kDa, respectively.

Figure 8:
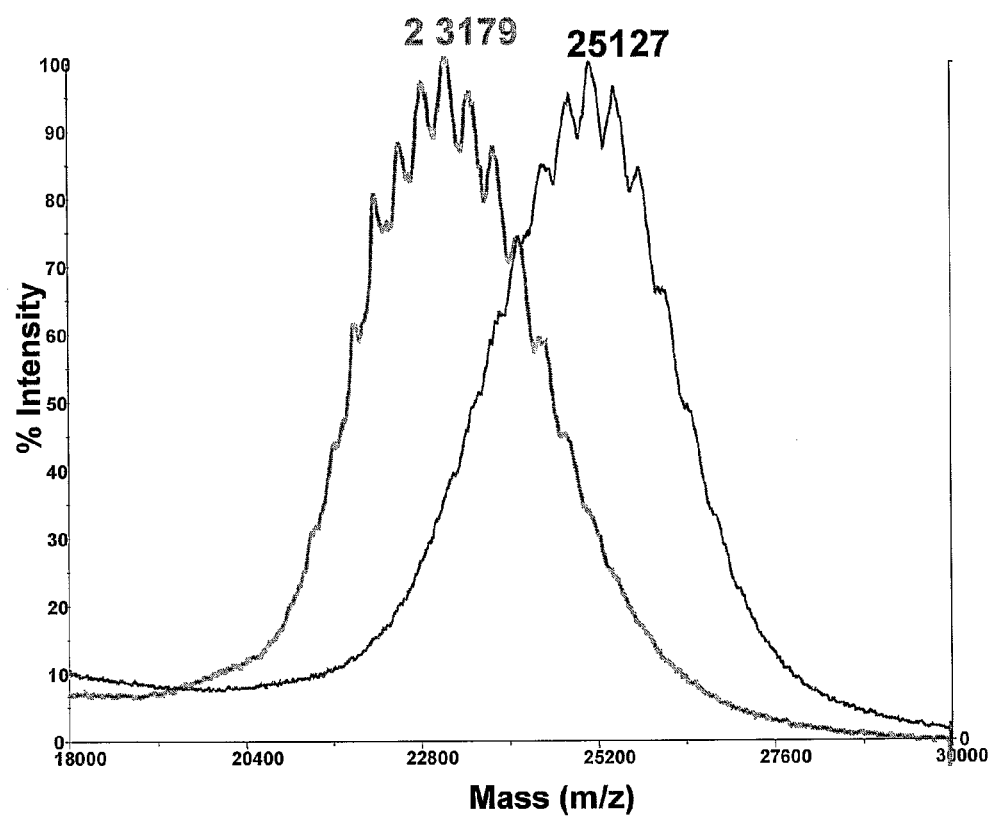

FIG. 8: Mass spectrum analysis of different purified rec-hIL-7 Glycoforms.
−23 kDa (23179 Da): Rec-hIL-7(CHO S, 2N+3N)
−25 kDa (25127 Da): Rec-hIL-7(CHO S, 3N)

Figure 9:
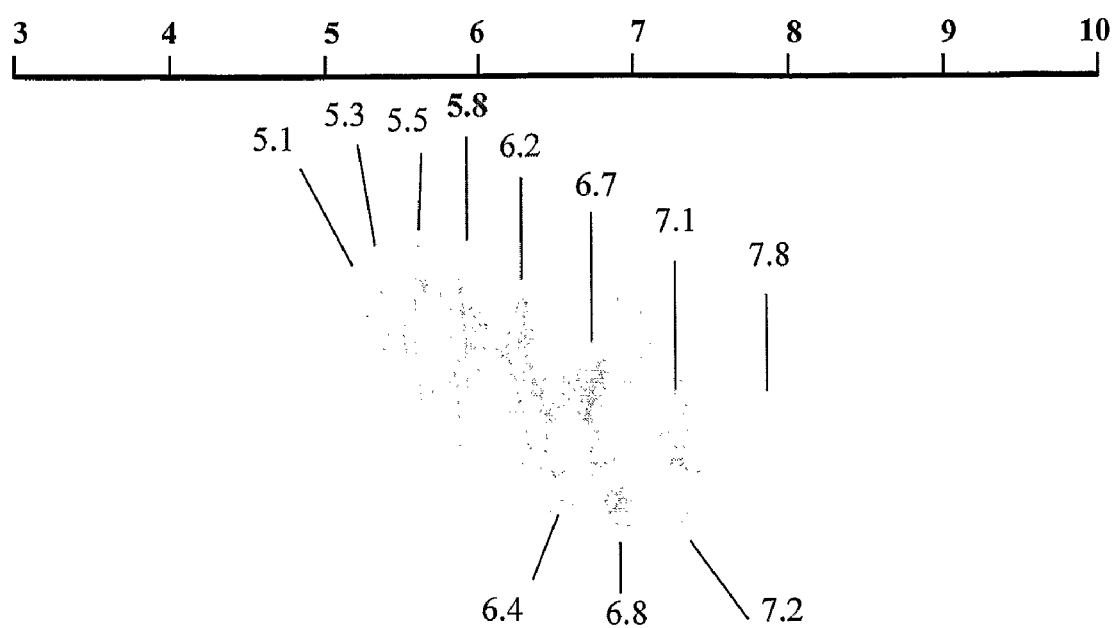

FIG. 9: 2D electrophoresis analysis of the purified recombinant hyperglycosylated human IL-7 polypeptide. After Iso Electric Focusing (pH range 3-10), glycoforms were separated on SDS PAGE under reducing conditions (Coomassie Blue Staining)

Figure 10:
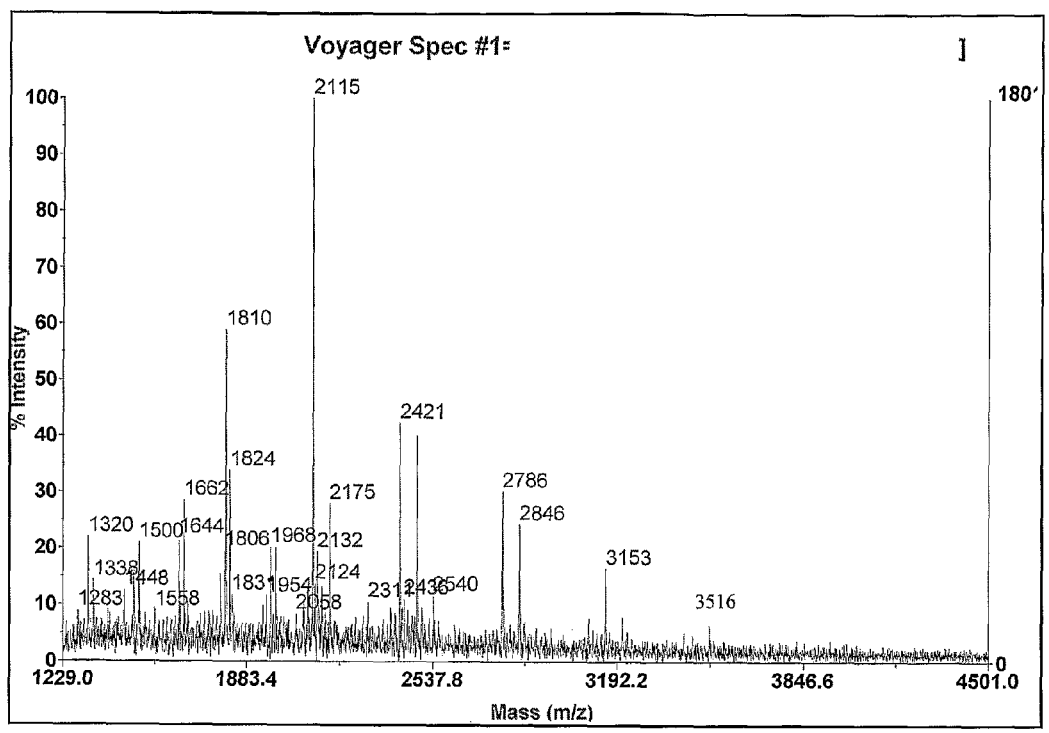

FIG. 10: Mass spectrum analysis of recombinant hIL-7 N-glycan complexity. Purified glycosylated hIL-7 samples were enzymatically digested with an endoglycosidase such as peptide-N-glycosidase F (PNGaseF, Roche). Released N-linked oligosaccharides, released protein sample by enzymatic digestion were separated from the peptide structure and analysed by MALDI-TOF Mass Spectrometry. The m/z values corresponding to each peak were searched against international databases and allowed accurate identification of the panel of N-Glycans on the hIL-7 molecule.

Figure 11:
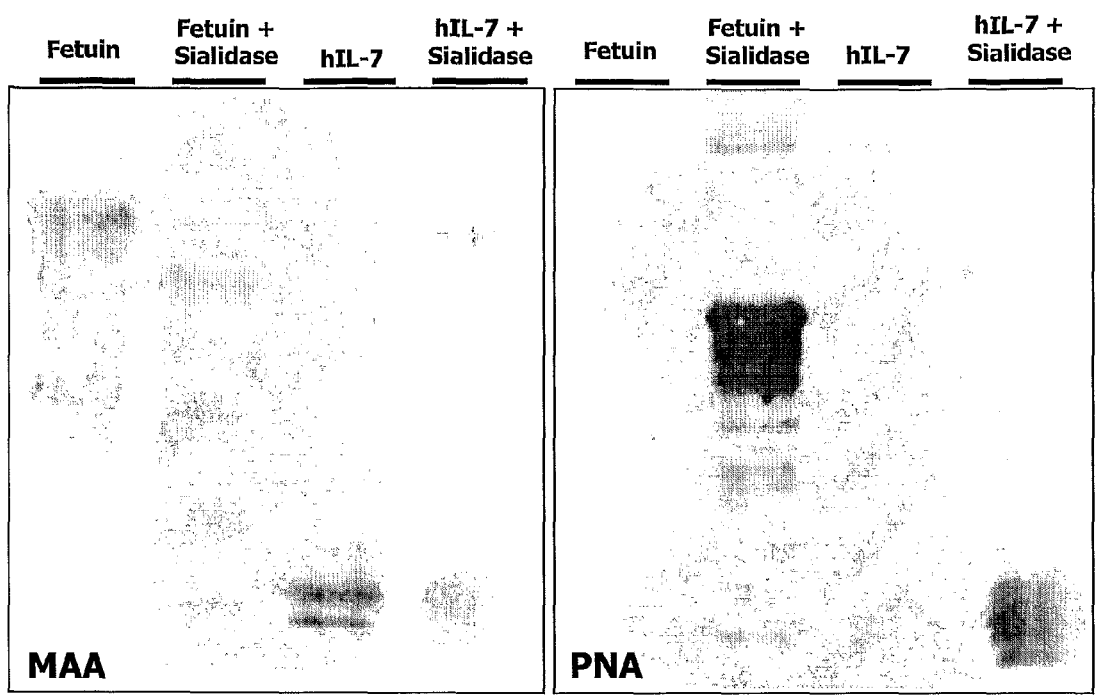

FIG. 11: Characterization of O-glycans on recombinant hIL-7, using specific lectins (lectin blot). After separation of protein samples and blotting to membrane, products were revealed with either one of the two lectins (MM, from *Maackia amurensis*, PNA, from *Arachis hypogea*). Lane 1: standard protein fetuin, a sialylated protein, Lane 2, fetuin treated with a sialidase, Lane 3, hIL-7, Lane 4, hIL-7 treated with sialidase.

Figure 12:
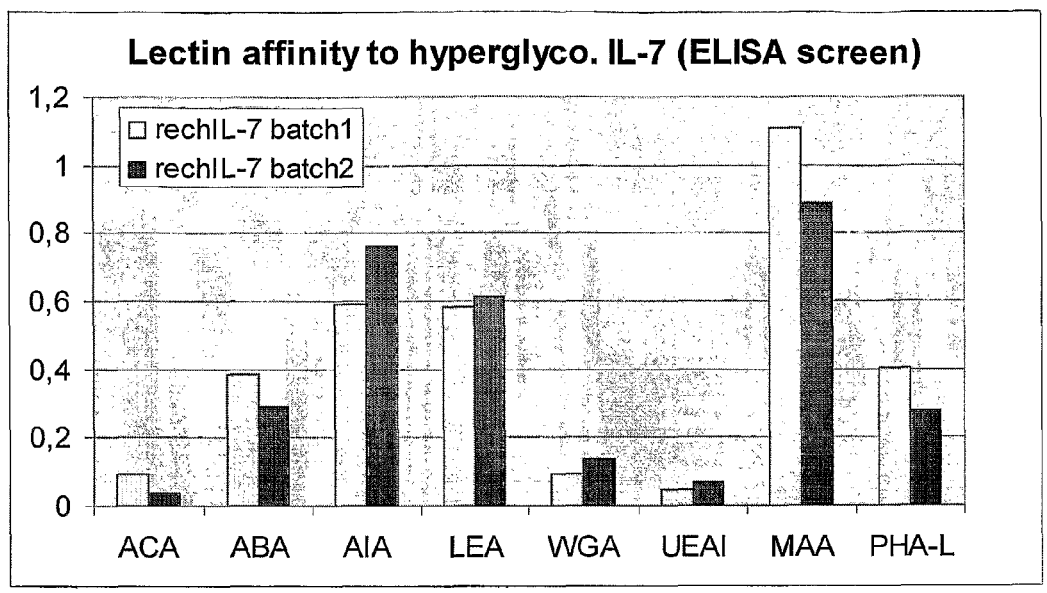

FIG. 12: Lectin affinity of hyperglycosylated IL-7 polypeptide (ELISA screen). Lectins (LEA from *Lycopersicon esculentum*, WGA from *Triticum vulgare*, UEA.I from *Ulex europeus*, MM from *Maackia amurensis*, ACA from *Amaranthus caudatus*, AIA from *Artocarpus intergrifolia*, ABA from *Agaricus bisporus*, PHA.L from *Phaseolus vulgaris* having)—cated plates used to bind identical amounts of recombinant purified hIL-7 preparations. Amounts of bound IL-7, depending on the lectin specificity to the glycan moieties, were revealed by a specific anti hIL-7 antibody (Ab) coupled to Biotin. The Lectin—IL-7—Ab sandwich was revealed with a streptavidin-peroxidase conjugate.

Figure 13:
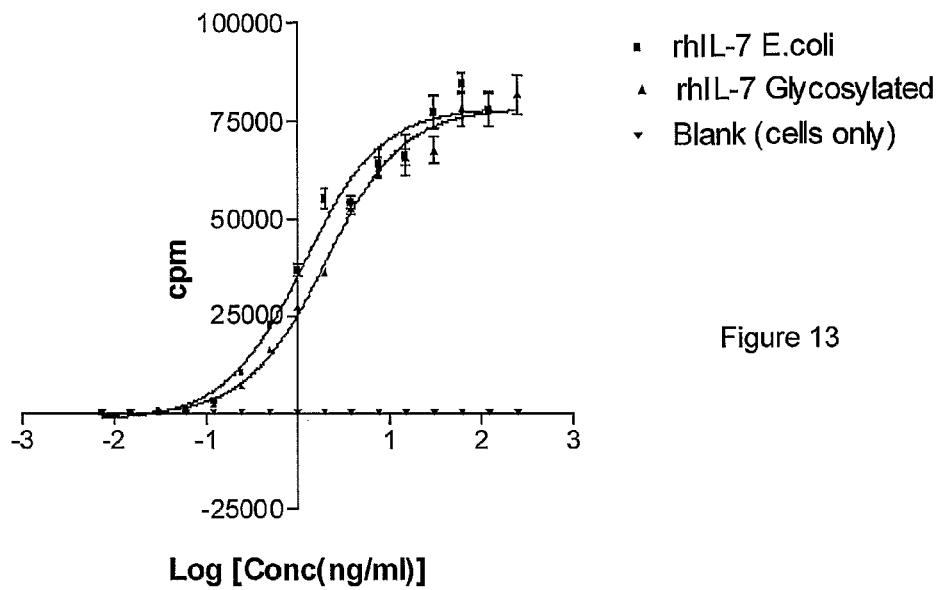

FIG. 13: Bioassay of recombinant human IL-7 activity. Dose-response kinetics of PB-1 cell growth induced by unglycosylated r-hIL-7 (expressed in *E. coli*) or highly glycosylated r-hIL-7 (produced in mammalian cells).

Figure 14:
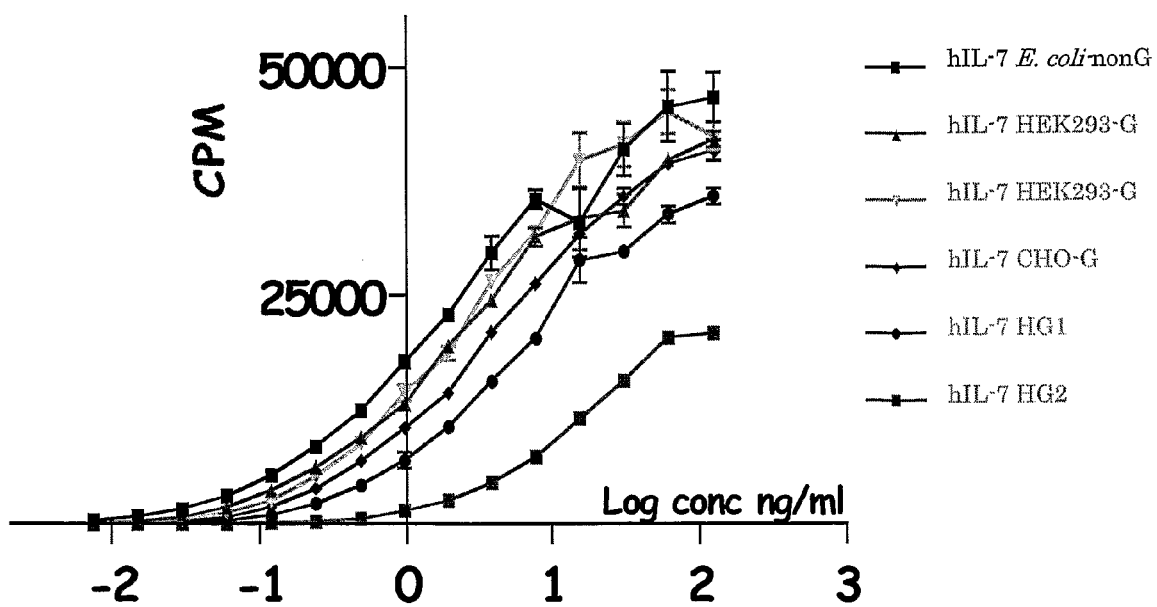

FIG. 14: Bioassay of recombinant human IL-7 activity. Dose-response kinetic data and curves obtained routinely in a typical bioassay: the PB-1 cell growth was induced by unglycosylated r-hIL-7 (expressed in *E. coli*), highly glycosylated or hyperglycosylated r-hIL-7 (produced in mammalian cells). (Data points represent the mean ±SD of triplicate determination).

DETAILED DESCRIPTION OF THE INVENTION

The present invention relates to hyperglycosylated IL-7 compositions, their manufacture and their uses in the pharmaceutical industry. The present invention, for the first time, shows that the activity and/or properties of IL-7 may be enhanced depending on the glycosylation profile of the polypeptide. The present invention also discloses, surprisingly and contrary to in vitro data, that the best in vivo activity can be achieved with IL-7 polypeptides having at least 2 to preferably 3 occupied N-linked glycosylation sites and one O-linked glycosylation site and maximized terminal sialylation of the oligosaccharide moieties. The present invention also discloses artificially created hyperglycosylated IL-7 polypeptides, which exhibit prolonged activity (thereby allowing a reduced administration frequency), and/or a decreased long-term immunogenicity. Considering the utility of IL-7, such polypeptides and compositions represent highly valuable and useful active molecules for use in regulating an immune response in a subject, including a human subject.

A first object of this invention thus resides in a hyperglycosylated IL-7 composition.

A further object of this invention relates to the use of hyperglycosylated IL-7 for the manufacture of a medicament consisting of said hyperglycosylated IL-7 and at least one pharmaceutically acceptable carrier or excipient, for treating a mammalian subject.

A further object of this invention is a method for causing or stimulating an immune response in a subject, comprising administering to the subject an effective amount of a hyperglycosylated IL-7 composition.

A further object of this invention relates to the use of a hyperglycosylated (and preferably highly sialylated) IL-7 composition for the manufacture of a medicament for causing or stimulating an immune response in a subject.

IL-7 Polypeptide

Within the context of the present invention, an "IL-7 polypeptide" designates a mammalian (e.g., human, simian, bovine, equine, feline or canine) IL-7 polypeptide. More preferably, the IL-7 polypeptide is a human IL-7 polypeptide, especially for uses as a therapeutic or vaccine. Alternatively, especially for use in non human primate experiments or in veterinary applications, the IL-7 polypeptide may be any other mammalian IL-7 polypeptides such as a simian IL-7 polypeptide or a canine polypeptide.

Preferred human IL-7 polypeptides of this invention comprise an amino acid sequence as described in EP 314 415 or in WO2004/018681 A2, as well as any natural variants and homologs thereof. The sequence of human IL-7 is also available on gene banks. The typical wild-type protein comprises 152 amino acids and, optionally, an additional N-terminal methionine residue (SEQ ID NO: 1). Variants thereof include, more preferably, natural allelic variants resulting from natural polymorphism, including SNPs, splicing variants, etc. In a specific embodiment, the term IL-7 polypeptide is meant to designate a polypeptide having the sequence of SEQ ID NO: 1 or natural variants thereof.

In a further embodiment, the IL-7 polypeptide is a canine IL-7 polypeptide. In this regard, the invention discloses, for the first time, the sequence of an isolated IL-7 polypeptide, which represents a further object of this application. In particular, the invention relates to an IL-7 polypeptide comprising amino acid sequence depicted in SEQ ID NO: 7, as well as any natural "variants," or homologs or distinctive fragments thereof. The term "variants" or "homologs" refer to polypeptides that differ from SEQ ID NO:7 by a deletion, substitution or addition of one or a limited number of amino acids. Preferably such variants or homologs show a percentage of identity that is superior to 85%, preferably superior to 90%, preferably superior to 95%, most preferably superior to 98% with SEQ ID NO:7.

The IL-7 polypeptide used in the present invention is preferably a recombinant IL-7. The term "recombinant", as used herein, means that the polypeptide is obtained or derived from a recombinant expression system, i.e., from a culture of host cells (e.g., microbial or insect or plant or mammalian) or from transgenic plants or animals engineered to contain a nucleic acid molecule encoding an IL-7 polypeptide. "Microbial" refers to recombinant proteins made in bacterial expression systems. "Mammalian" refers to recombinant glycoproteins made in mammalian expression systems. As will be discussed below, all of these host cells should preferably express either naturally or after transgenesis an appropriate glycosyltransferase and/or sialyltransferase gene. IL-7 polypeptide can also be glycosylated through the use of appropriate in vitro or in vivo glycosyltransferase and/or sialyltransferase molecules, or by grafting oligosaccharide structures.

A specific example of a human IL-7 polypeptide is a polypeptide of SEQ ID NO: 1 comprising the disulfide bridges Cys2-Cys92; Cys34-Cys129 and Cys47-Cys141.

Also, IL-7 polypeptides of the present invention may comprise the sequence of a mature IL-7 polypeptide, or further comprise additional amino acid residues, such as a secretion peptide for instance. Preferred examples of such secretion peptides include, without limitation, a signal peptide selected from the group consisting of the EPO signal peptide, SEAP signal peptide, IgGkappa signal peptide, Lactotransferin/vitronectin signal peptide, VIP/vitronectin signal peptide and cytostatin bis signal peptide. The sequence of these signal peptides is set forth, respectively, in SEQ ID NO 13 to 18. In a specific embodiment, the signal peptide is a hybrid construct made by the inventors, between sequences derived from the EPO and IL-7 signal peptides. The sequence of this signal peptide, termed EPy7 or EP7, is set forth in SEQ ID NO: 19 and represents a particular object of this invention.

Hyperglycosylated IL-7 and Compositions

Within the context of the present invention, the term "hyperglycosylated IL-7" designates an IL-7 polypeptide having at least three occupied glycosylation sites, i.e., having at least three glycosylated amino acid residues.

A "glycosylation site" designates any amino acid residue or region in a polypeptide which is subject to glycosylation, i.e., the attachment of a carbohydrate structure. Such sites are typically N-glycosylation sites (i.e., any amino acid residue or region in a polypeptide which allows the attachment of a carbohydrate structure through N-linkage) and/or O-glycosylation sites (i.e., any amino acid residue or region in a polypeptide which allows the attachment of a carbohydrate structure through O-linkage). Consensus sequences for glycosylation sites are known per se in the art. As an illustration, a consensus N-glycosylation site typically has the following structure: Asn-X-Ser/Thr, where X is any amino acid except Proline. As will be disclosed below, such glycosylation sites may be either naturally present within an IL-7 polypeptide sequence and/or artificially added or created within said sequence.

The term "hyperglycosylated IL-7 composition" designates an IL-7 composition in which at least 80% of IL-7 polypeptides have at least three occupied glycosylation sites, i.e., having at least three glycosylated amino acid residues. Preferably, such a composition comprises at least 80% of IL-7 polypeptides that are glycosylated, at least, at three N-glycosylation sites(s) and, optionally, at one O-glycosylation site. Such a composition is most preferably essentially devoid of un- or mono-glycosylated IL-7 polypeptides, and thus comprises at most 20% of bi-glycosylated IL-7 polypeptides. In a preferred embodiment, a hyperglycosylated IL-7 composition designates an IL-7 composition in which at least 90% of IL-7 polypeptides are glycosylated at three N-glycosylation sites(s) and, optionally, at one O-glycosylation site. Such a composition is most preferably essentially devoid of un- or mono-glycosylated IL-7 polypeptides, and thus comprises at most 10% of bi-N-glycosylated with or without mono-O-glycosylated IL-7 polypeptides.

IL-7 primary amino acid sequence comprises three putative N-glycosylation sites, namely Asparagine (Asn) residues at positions 70, 91 and 116 (with respect to the human wild type sequence, see SEQ ID NO: 1). Furthermore, the present invention shows that the IL-7 sequence also contains one O-glycosylation site, namely Threonine (Thr) residue at position 110. In a particular embodiment, a hyperglycosylated IL-7 polypeptide of the present invention is an IL-7 polypeptide having the above three N-glycosylation sites occupied associated or not to one occupied O-glycosylation site and a hyperglycosylated IL-7 composition is an IL-7 composition in which at least 80% of IL-7 polypeptides are glycosylated at the above N-glycosylation sites and, optionally, also at the O-glycosylation site.

In a particular embodiment, a hyperglycosylated IL-7 polypeptide may comprise additional artificially added or created glycosylation sites. Accordingly, a hyperglycosylated IL-7 polypeptide of the present invention is an IL-7 polypeptide having at least three N-glycosylation sites and one O-glycosylation site occupied, said sites being either naturally-occurring and/or artificially added/created; and a hyperglycosylated IL-7 composition is an IL-7 composition in which at least 80% of IL-7 polypeptides are glycosylated at four glycosylation sites(s) at least, said sites being either naturally-occurring and/or artificially added/created.

In this regard, the present invention now discloses IL-7 polypeptides having a modified amino acid sequence, wherein said sequence comprises at least one artificially created glycosylation site. According to particular embodiments, the IL-7 polypeptides of this invention comprise 1, 2, 3 or 4 artificially created glycosylation sites, more preferably 1, 2 or 3; even more preferably 1 or 2.

The artificially created glycosylation sites are preferably N-linked glycosylation sites. Consensus N-glycosylation sites typically have the following structure: Asn-X-Ser/Thr, where X is any amino acid except Proline.

The glycosylation sites may be created or added chemically from assembled synthetic oligonucleotides or using several techniques including mutagenesis methods at various positions within IL-7 primary amino acid sequence, and following techniques known per se in the art. Because the modified IL-7 polypeptide shall retain the ability to bind an IL-7 receptor, the glycosylation site(s) is (are) most preferably created within region(s) or domain(s) of the IL-7 polypeptide sequence which do(es) not alter the ability of IL-7 to bind an IL-7 receptor. More preferably, the site(s) is (are) introduced outside of the alpha helices of the polypeptide, preferably except at immediate proximity of the glycine residues. Preferably, they are introduced in the most flexible region, avoiding regions that are more rigid and important for tertiary structure of the polypeptide. Preferably, the creation of a glycosylation site does not affect any Cystein residue involved in a disulfide bridge (e.g., Cys 2, 34, 47, 92, 129 and 141), nor any critical residue involved in the interaction of IL-7 polypeptide with its cognate receptor (e.g., Ser 19, Leu 23 and 77, Tyr 12, Val 15, Gln 22, Lys 81 and Glu 84), nor any conserved residue involved in the activity of the polypeptide (e.g., Arg 133, Gln 136, Glu 137, Lys 139 and 144, Thr 140 and Asn 143). The glycosylation sites are typically created by mutation, deletion or addition of one or several amino acid residues within the primary sequence of a reference IL-7 polypeptide, to create a typical consensus glycosylation site.

In a particular embodiment, the present invention relates to IL-7 polypeptides comprising the sequence of a human (or mammalian) IL-7 polypeptide comprising one or several amino acid modifications selected from Lys28Asn-Ile30Ser-Ile30Thr-Ile30Asn-Ser32Thr-Leu35Ser-Leu35Thr-Glu38Ser-Glu38Thr-Phe39Ser-Phe39Thr-Phe42Ser-Phe42Thr-Glu52Ser-Glu52Thr-Val82Asn-Glu84Thr-Glu84Ser-Lys97Asn-Arg99Thr-Arg99Ser-Ala102Asn-Leu104Thr-Leu104Ser-Leu104Asn-Glu106Thr-Glu106Ser-Leu128Ser-Leu128Thr-Ile145Asn-Met147Thr-Met147Ser-Met147Asn-Thr149Ser (or from corresponding positions in other mammalian IL-7 polypeptides).

Specific examples of (human) IL-7 polypeptides of this invention comprise the amino acid modifications disclosed in Table 1 below:

TABLE 1

| IL-7 polypeptide analog | amino acid changes |
|---|---|
| HG28a | Lys28Asn; Ile30Ser |
| HG28b | Lys28Asn; Ile30Thr |
| HG30 | Ile30Asn; Ser32Thr |
| HG33a | Leu35Ser |
| HG33b | Leu35Thr |
| HG36a | Glu38Ser |
| HG36b | Glu38Thr |
| HG37a | Phe39Ser |
| HG37b | Phe39Thr |
| HG40a | Phe42Ser |
| HG40b | Phe42Thr |
| HG50a | Glu52Ser |
| HG50b | Glu52Thr |
| HG82a | Val82Asn; Glu84Ser |
| HG82b | Val82Asn; Glu84Thr |
| HG97a | Lys97Asn; Arg99Ser |
| HG97b | Lys97Asn; Arg99Thr |
| HG102a | Ala102Asn; Leu104Ser |
| HG102b | Ala102Asn; Leu104Thr |
| HG104a | Leu104Asn; Glu106Ser |
| HG104b | Leu104Asn; Glu106Thr |
| HG126a | Leu128Ser |
| HG126b | Leu128Thr |
| HG145a | Ile145Asn; Met147Ser |
| HG145b | Ile145Asn; Met147Thr |
| HG147 | Met147Asn; Thr149Ser |

The above amino acid modifications create N-glycosylation sites without substantially altering the binding affinity of IL-7, thereby creating improved IL-7 polypeptides according to the present invention.

The term "without substantially altering the binding affinity" means that the binding affinity is not altered or may be reduced without impacting the in vivo effects resulting from the interaction with the receptor. When quantified in vitro, the binding affinity may be reduced by less than 50%, preferably less than 40%, preferably less than 30%, preferably less than 20%, preferably less than 5%.

Also, the above modifications can be combined to create several additional glycosylation sites within an IL-7 polypeptide of this invention. In this regard, the invention relates to any biologically active IL-7 polypeptide having the primary sequence of (human or mammalian) interleukin-7 modified by the addition of at least from one to four additional (N-linked) glycosylation sites. A further preferred embodiment of this invention is a biologically active IL-7 polypeptide comprising the primary sequence of interleukin-7 comprising one or two additional (N-linked) glycosylation sites.

Most preferred IL-7 polypeptides of this invention are biologically active, i.e., they are capable of binding to an interleukin-7 receptor and show in vitro activity in a specific bioassay and/or have an increased mean residence time (MRT) in vivo.

Comparison of activities between the non glycosylated standard and the hyperglycosylated IL-7 was addressed in a dose/response bioassay study in which an ED50 value corresponds to a dose equal to one half of maximal activity. Hyperglycosylation, usually leads to decreased activity in the bioassay, which does not translate into decreased in vivo activity. In the present situation, the extended kinetic profile will in fact improve the in vivo activity.

In spite of the fact that ED50 does not reflect activity of the IL-7 in vivo, it allows comparison between different samples with the same level of glycosylation. In this frame, typical ED50 values for a non glycosylated standard were ranging between 0.5 to 2.0 ng IL-7/ml while hyperglycosylated ED50 values were ranging between 1.5 to 3.5 ng hyperglycosylated IL-7/ml.

The hyperglycosylated IL-7 polypeptides of the invention show an improved stability, and an in vivo extended half-life and mean residence time in mammalian hosts. The term "improved stability", "extended half-life and mean residence time" is to be understood in comparison to non-glycosylated forms. Preferably the increase of half-life is at least about 3×, preferably at least about 5 to 20×. Mean residence time (MRT) means the average of the residence time of each IL-7 molecule in the blood of patients after initial dosing. Preferably, the increase of MRT is at least about 2×, or preferably at least about 4 to 10× compared to the MRT of non-glycosylated forms.

For instance the plasmatic half-life of the hyperglycosylated form was shown to be in the range of 30 to 40 hours, whereas the plasmatic half-life of the non-glycosylated form is usually 5 to 8 hours (when both forms are administered in the same conditions, i.e. in one injection, subcutaneously).

The mean residence time (MRT) was around 40 hours versus around 10 hours with the non glycosylated form.

It should be understood that the invention also encompasses any distinctive fragment of an IL-7 polypeptide of this invention, i.e., any fragment comprising an amino acid modification as disclosed above, or any fragment comprising an artificially created glycosylation site as disclosed above. Such fragments typically contain at least 5 amino acid residues, typically at least 8, 9, 10, 11, 12 or 15 residues, and may contain up to 20, 30, 40, 50 or more consecutive amino acid residues. Such fragments may be used as antagonists or as immunogens, to generate specific antibodies.

Also, while the above amino acid positions have been given by reference to the human IL-7 polypeptide sequence, it should be understood that the present invention also encompasses IL-7 polypeptides having the primary sequence of mammalian IL-7 modified by homologous mutations in mammalian sequences based on sequence alignment against human sequence.

A preferred embodiment of this invention relates to new biologically active IL-7 polypeptides comprising one or several amino acid modification(s) selected from the group consisting of:

Phe39Ser-Phe39Thr-Phe42Ser-Phe42Thr-Leu104Asn-Glu106Thr-Glu106Ser-Leu128Ser-Leu128Thr-Met147Asn and a combination thereof, or a distinctive fragment thereof.

Most preferred modified IL-7 polypeptides of this invention are disclosed in Table 2 below:

TABLE 2

| IL-7 polypeptide analog | amino acid changes |
|---|---|
| HG37a | Phe39Ser |
| HG37b | Phe39Thr |
| HG40a | Phe42Ser |
| HG40b | Phe42Thr |
| HG104a | Leu104Asn; Glu106Ser |
| HG104b | Leu104Asn; Glu106Thr |
| HG126a | Leu128Ser |
| HG126b | Leu128Thr |
| HG147 | Met147Asn; Thr149Ser |

A further particular object of this invention is a hyperglycosylated IL-7 polypeptide comprising a primary amino acid sequence as disclosed above.

Oligosaccharide Units

The structure and number of oligosaccharide units attached to a particular glycosylation site in a hyperglycosylated IL-7 polypeptide of this invention can be variable. These may be, for instance, N-acetyl glucosamine, N-acetyl galactosamine, mannose, galactose, glucose, fucose, xylose, glucuronic acid, iduronic acid and/or sialic acids.

More preferably, hyperglycosylated IL-7 polypeptides comprise (or are enriched in) N-linked and/or O-linked carbohydrate chain(s) selected from:
a) a mammalian type sugar chain, preferably of the type expressed by CHO cells;
b) a sugar chain comprising a complex N-carbohydrate chain (e.g., a triantenary or biantenary structure), more preferably containing high mannose and acetylglucosamine molecules and high terminal sialic acid residues;
c) a sugar chain comprising an O-carbohydrate chain without and preferably with a terminal sialic acid residue;
d) a sugar chain sialylated by alpha-2,6-sialyltransferase or alpha-2,3-sialyltransferase; and/or
e) a sialylated sugar chain displaying between 3 to 30 sialyl-N-acetylgalactosamine, preferably 7 to 23.

Particularly preferred carbohydrate chain(s) comprise a triantenary or biantenary structure with partial or complete terminal sialylation. Further preferred carbohydrate chains comprise triantenary structures and tri or bi-sialylation, and/or a diantenary structure with disialylation. Examples of such carbohydrates are disclosed in Table 4, including motifs #2420, 2623, 2785 and 3092.

According to a further specific embodiment, the hyperglycosylated interleukin-7 polypeptide of this invention has an average isoelectric point inferior to 6.5 and an average apparent molecular weight superior to 27 kDa, between 28 KDa and 65 KDa (theoretical for a 7N+1O glycosylation), preferably between 28 KDa and 35 KDa (as shown for a 3N+1O glycosylation), by gel electrophoresis (confirmed by Western blot) which is translated to 25 kDa by mass spectrometry analysis.

In a particular embodiment, the hyperglycosylated IL-7 polypeptide of this invention is produced by a mammalian glycosylation mutant that stably expresses α2,6 sialyltransferase and presents a deficiency in CMP-Neu5Ac Hydrolase activity, preferably a CHO glycosylation mutant. Such glycosylation typically includes N-acetyl glucosamine, N-acetyl galactosamine, mannose, galactose, glucose, fucose, xylose, glucuronic acid, iduronic acid and/or sialic acids.

In an other embodiment, the hyperglycosylated IL-7 polypeptide is produced by recombinant technology in a human host cell, which may be selected from human stromal or epithelial cell lines, HEK-293 (Human Embryonic Kidney), HER (Human Embryonic Retina), HEK (Human Epidermal Keratinocytes), human thymus or human cortical epithelial cell lines, human bone marrow or human bone marrow stromal cell lines.

Most preferred hyperglycosylated interleukin-7 polypeptides of this invention display the following feature(s):
a) they have improved secretion profile and production rate in recombined productive cell lines; and/or
b) they contain a high degree of sialic acid residue per IL-7 polypeptide, leading to decrease isoelectric point value and to improve mean residence time; and/or
c) they are protected from inter-molecular aggregation; and/or
d) they have reduced susceptibility to proteolysis; and/or
e) they contain masked antigenic sites, reflecting reduced immunogenic liability, reduced vulnerability to APC (antigen presenting cells) capture, processing and presentation through a MHCII molecule; and/or
f) they have increased chemical stability; and/or
g) they have an extended biological half-life in vivo (Long acting isoform of IL-7) compared to the unglycosylated parent peptide; and/or
h) they have an increased in vivo pharmacological activity compared to unglycosylated parent protein, mostly due to a better mean residence time (MRT); and/or
i) they permit less frequent dosing schedule, from three/four times a week down to two or once a week or once every fortnight for the more long acting products; and/or
j) they display an improved pharmacokinetic profile (decreased peak concentration and improved mean residence time) and/or
k) they display an average molecular weight above 25 KDa as determined from Mass Spectrometry analysis or 27 KDa as determined from SDS-PAGE analysis and an average isoelectric point below 6.5.

The polypeptides of this invention may be in the form of a monomer, or associated or complexed with a particular compound of choice. In this regard, in a particular embodiment, the IL-7 conformer is associated to the hepatocyte growth factor ("HGF"), as a heterodimer. The heterodimer may be obtained chemically, by complexation or by recombinant technology (i.e., by genetic fusion).

In an other particular embodiment, the IL-7 polypeptide is functionally attached to a Fc portion of an IgG heavy chain, typically through a peptide hinge region. Such fusion molecules have potentially increased stability and half-life in vivo. The IgG moiety is most preferably a human IgG1 or IgG4.

In an other particular embodiment, the IL-7 polypeptide is functionally associated to a human serum albumin ("HSA") or a portion of a HSA, as a fusion protein. Such fusion molecules have potentially increased stability and prolonged half-life in vivo.

A further object of this invention is a hyperglycosylated IL-7 composition. Such compositions preferably comprise at least 80%, preferably between 80% and 95%, IL-7 polypeptides which are glycosylated on at least three distinct amino acid residues, which may be naturally present within an IL-7 polypeptide sequence (e.g. consensus N-linked and O-linked carbohydrate sites) and/or artificially created glycosylation sites(s), as discussed above.

According to particular, specific, embodiments, the invention relates to hyperglycosylated IL-7 compositions comprising:
a) a majority (>80%, preferably more than 90%, most preferably more than about 95%) of interleukin-7 glycosylated on the 3 consensus N-linked carbohydrate sites (Asn 70/91/116) and further glycosylated or not on 1 O-linked carbohydrate site (Thr 110); preferably, the composition contains a minority (<20%, preferably less than about 10%) of interleukin-7 glycosylated on 2 consensus N-linked carbohydrate sites only (associated or not to 1 O-linked carbohydrate site) and/or is essentially devoid of mono- or unglycosylated protein; or
b) a majority (>80%, preferably more than 90%, most preferably more than about 95%) of a biologically active interleukin-7 analog, having the IL-7 primary amino acid sequence modified to introduce one additional site of glycosylation, glycosylated on 4 N-linked carbohydrate sites and further glycosylated or not on 1 O-linked carbohydrate site (Thr 110); preferably the composition contains a minority of the same analog (<20%, preferably less than about 10%) glycosylated on 3 or 2

N-linked carbohydrate sites only (associated or not to 1 O-linked carbohydrate site) and/or is essentially devoid of mono- or unglycosylated protein; or c) a majority (>80%, preferably more than 90%, most preferably more than about 95%) of an interleukin-7 biologically active analog, having the IL-7 primary amino acid sequence modified to introduce two additional sites of glycosylation, glycosylated on 5 N-linked carbohydrate sites and further glycosylated or not on 1 O-linked carbohydrate site (Thr 110); preferably the composition contains a minority of the same analog (<20%, preferably less than about 10%) glycosylated on 4, 3 or 2 N-linked carbohydrate sites only associated or not to 1 O-linked carbohydrate site and/or is essentially devoid of mono- or unglycosylated protein; or d) a majority (>80%, preferably more than 90%, most preferably more than about 95%) of an interleukin-7 biologically active analog, having the IL-7 primary amino acid sequence modified to introduce three additional sites of glycosylation, glycosylated on 6 N-linked carbohydrate sites and further glycosylated or not on 1 O-linked carbohydrate site (Thr 110); preferably the composition contains a minority of the same analog (<20%, preferably less than about 10%) glycosylated on 5, 4, 3 or 2 N-linked carbohydrate sites only associated or not to 1 O-linked carbohydrate site and/or is essentially devoid of mono- or unglycosylated protein; or e) a majority (>80%, preferably more than 90%, most preferably more than about 95%) of an interleukin-7 biologically active analog, having the IL-7 primary amino acid sequence modified to introduce four additional sites of glycosylation, glycosylated on 7 N-linked carbohydrate sites and further glycosylated or not on 1 O-linked carbohydrate site (Thr 110); preferably the composition contains a minority of the same analog (<20%, preferably less than about 10%) glycosylated on 6, 5, 4, 3 or 2 N-linked carbohydrate sites only associated or not to 1 O-linked carbohydrate site and/or is essentially devoid of mono- or unglycosylated protein.

The invention also relates to pharmaceutical compositions comprising the above compositions as the active substance.

Nucleic Acids

A further object of this invention resides in a nucleic acid molecule encoding an IL-7 polypeptide as discussed above. The nucleic acid molecule may be any DNA or RNA molecule, typically a cDNA molecule.

A specific object of this invention is a nucleic acid comprising nucleotide residues 79 to END of SEQ ID NO: 2, as well as distinctive fragments and the complementary strand thereof.

A further object of this invention is a nucleic acid comprising SEQ ID NO: 4, as well as any distinctive fragment thereof, variants thereof (having at least 90% identity with SEQ ID NO: 4), and the complementary strand thereof.

A further object of this invention is a nucleic acid comprising SEQ ID NO: 6, as well as any distinctive fragment thereof, variants thereof (having at least 90% identity with SEQ ID NO: 6) and the complementary strand thereof. A specific object of this invention is a nucleic acid comprising nucleotide residues 79 to END of SEQ ID NO: 6, as well as variants thereof (having at least 90% identity with SEQ ID NO: 6) and the complementary strand thereof. The invention also encompasses a polypeptide encoded by such sequences (e.g., SEQ ID NO: 7).

The term "variant" as used above in relation to a nucleic acid more specifically designates a nucleotide sequence that hydridizes to the reference sequence under stringent condition and/or encodes a polypeptide having the same type of activity as the polypeptide encoded by the reference sequence. Most preferred variants exhibit at least between 92 and 99% (e.g., 92%, 93%, 94%, 95%, 96%, 97%, 98% or 99%) identity with the reference sequence.

A further specific object of this invention is a nucleic acid comprising the sequence of:

CTG AAT AAC GAA ACT AAC SEQ ID NO: 8

AAC TTC ACT AAG SEQ ID NO: 9

GCC AAC GGT ACC SEQ ID NO: 10

CTG AAC GAC AGC TGT SEQ ID NO: 11, or

ATC TTG AAC GGG SEQ ID NO: 12, or a combination thereof.

Specific examples of nucleic acids of this invention comprise the nucleotide sequence as set forth in any one of SEQ ID NOs: 8 to 12.

A further object of this invention resides in a cloning and/or expression vector comprising a nucleic acid molecule as defined above. The vector may be any prokaryotic or eukaryotic vector, typically an eukaryotic vector, and may be selected from a plasmid, cosmid, viral vector, artificial chromosome, etc. The vector may comprise any regulatory sequence allowing proper expression of the coding nucleic acid in a selected host cell, e.g., a promoter, terminator, polyA, origin of replication, integration region (e.g., homologous region), intron, UTR sequences, marker gene, etc.

A particular object of this invention is an expression vector comprising a nucleic acid molecule as defined above, including a signal peptide, operably linked to regulatory elements allowing expression of said nucleic acid in a mammalian host or host cell.

Preferred regulatory elements include a promoter, which may be selected, without limitation, from viral, cellular and synthetic promoters, including constitutive, tissue-specific or regulated promoters, in particular from the group consisting of the CMV promoter, E1Fa promoter and metallothionein promoter. Further regulatory elements that may be contained within the vectors of this invention include, without limitation, a Bcl-2 gene, UTR sequences and MAR sequences.

In a preferred embodiment, the vector is an episomic expression vector.

The above nucleic acids and vectors may be used for instance to produce recombinant mammalian IL-7 polypeptides in various competent host or host cells, as well as for gene therapy purposes.

Another object of this invention resides in a recombinant host cell comprising a nucleic acid or a vector as disclosed above. Such a recombinant cell may be prokaryotic or, more preferably, eukaryotic, such as a yeast, insect, plant or mammalian cell, for instance.

In a preferred embodiment, the host cell is a mammalian cell, preferably selected from PERC6, NSO cells and BHK cells, preferably CHO cells; or a human cell line. The vectors, constructs and recombinant cells will be disclosed in more details, but not limited to, in a subsequent section of this application.

Drug Substance and Pharmaceutical Compositions

Another object of this invention resides in a drug substance comprising as the desired product, an IL-7 polypeptide as described above, typically a hyperglycosylated IL-7 polypeptide. More preferably, the drug substance contains less than about 10% of un- or mono-glycosylated IL-7 polypeptide and/or is essentially devoid of product-related impurities.

The invention also relates to the use of a drug substance as described above in the manufacture of a medicament ("drug product") or pharmaceutical composition.

A preferred drug substance is further substantially free of process related impurities.

Within the context of the present application, the term "drug substance" refers to a product suitable for use as the active principle of a medicament. The "drug substance" according to this invention is, by nature, a complex product, i.e., as a result of its production method (e.g., recombinant DNA technology).

The present invention now discloses that, in order to produce efficient therapeutic and vaccine enhancement effects, an IL-7 drug substance or pharmaceutical composition should contain, as the major molecular species, a hyperglycosylated IL-7 polypeptide composition.

The term "substantially free", as used herein, indicates that the drug substance contains no significant or adverse amount of product-related impurities and process-related impurities. More specifically, the drug substance should contain less than 5%, more preferably less than 3%, even more preferably less than 2% of product-related impurities and process-related impurities. Most preferred drug substances contain less than about 1% of product-related impurities and only trace amount of process-related impurities.

IL-7 product-related substances designate IL-7 molecular variants, which include, for example, active or inactive peptide or polypeptide fragments of IL-7.

IL-7-related impurities include, for example, human IL-7 polypeptides comprising mono or bi-disulfide bridges, truncated IL-7, deamidated recombinant IL-7, dimeric or multimeric protein comprising IL-7, oxidized methionine form or a combination thereof.

Whatever their biological activity, these IL-7 molecular variants and IL-7-related impurities should be strictly minimized or discarded from the drug substance.

Process related impurities include, DNA, endotoxins, cell debris, viruses, etc.

A preferred drug substance is thus a drug substance wherein the total amount by weight of a hyperglycosylated IL-7 composition comprises at least 95% by weight, preferably at least 98% by weight, more preferably at least 99.5% by weight of a hyperglycosylated IL-7 composition according to the invention.

The invention also relates to a pharmaceutical composition comprising an effective amount of a drug substance or hyperglycosylated IL-7 composition as described above and one or more pharmaceutically compatible or acceptable carriers, excipients or diluents.

The invention shows that pharmaceutical compositions comprising a hyperglycosylated IL-7 composition as described above clearly increase the vaccine properties of IL-7 and its capacity to stimulate antigen-specific immune responses.

The pharmaceutically compatible or physiologically acceptable carrier, excipient or diluent may be selected from neutral to slightly acidic, isotonic, buffered saline, solutions or suspensions and more preferably from sucrose, trehalose, and amino acid. The pharmaceutically compatible carrier is preferably contained in an appropriate buffer to form an isotonic solution. An appropriate buffer has preferably a pH range comprised between 4.5 to 7.5, preferably 5.0 to 7.0, even more preferably of about 5.5 and is preferably an organic salt selected from a sodium citrate buffer or an ammonium acetate buffer. The pharmaceutical composition may be in the form of a suspension, solution, gel, powder, solid, etc. The composition is preferably a liquid form.

The composition may comprise stabilizing agents, such as sugar, amino acids, proteins, surfactants, etc. The composition may comprise any saline solution, including phosphates, chloride, etc.

A particular pharmaceutical composition according to the invention comprises, in addition to the active drug substance, a protein and/or a surfactant. This presence of a protein, or any other high molecular weight molecule of natural origin, reduces exposition of IL-7 to the host immune system and therefore avoids secondary effects. More preferably, the protein is non immunogenic in the subject, such as any protein of human origin. A most preferred example of protein is human serum albumin. The surfactant may be selected from known surfactants such as Polysorbate products, preferably Tween20™ or Tween80™. A specific composition of this invention comprises human serum albumin (preferably 2 to 5 mg/ml) or polysorbate (Tween 20 or 80 (typically 0.005%)) or any other substance such as a tensioactive substance or amino acid (e.g., arginine, glutamate, or a mixture of arginine and glutamate) or sugar (e.g., sucrose, trehalose, sorbitol), capable of preventing IL-7 immunogenicity due to protein aggregation and/or local persistence of the drug product at injection site after administration of the composition.

In this respect, particular objects of this invention reside in pharmaceutical compositions containing a hyperglycosylated interleukin-7 composition at a concentration of about 1 mg/ml to 50 mg/ml, preferably of about 3 mg/ml to 20 mg/ml. Preferably, the effective amount of glycosylated interleukin-7 to be administered is comprised between about 10 to 200 µg/kg/week, preferably between about 10 to 60 µg/kg/week, e.g. for treatment or prevention of infectious diseases.

In view of the improved properties of the polypeptides and compositions of this invention, the pharmaceutical compositions need to be administered less frequently than prior art compositions or products in an equivalent amount to obtain comparable therapeutic effects. More specifically, in a typical embodiment, the compositions are administered 3 times per week, 2 times per week, once a week, once every other week, once a month, once or twice before vaccination or before and after vaccination. A preferred dosing regimen consists in administering the pharmaceutical composition once every 7, 10 or 14 days.

Preferred administration routes are parenteral routes. The parenteral route is preferably an intra-tumoral, more preferably an intravenous or a sub-cutaneous administration. It includes also intra-arterial, intra-peritoneal or intramuscular injections. It should be understood, however, that any other suitable administration route may be contemplated depending upon the health status and the reactivity of the patient.

In a particular embodiment, the administration route is the oral route. In comparison to other polypeptide hormones, oral route is indeed acceptable for hyperglycosylated IL-7 because of the exceptional stability of this protein. The compositions of the invention are then preferably in a solid form, such as a tablet or a powder or a capsule, or in a form of a liquid, such as a syrup or an emulsion, prepared in an appropriate pharmaceutically acceptable carrier. Preferably the carrier itself is stable in the gastro-intestinal tract and in the circulatory system and exhibits an acceptable plasma half-life.

Gastric acid-resistant capsules, such as gastric acid-resistant capsules containing a micro-emulsion or liposome formulation of hyperglycosylated IL-7 polypeptide, are advantageous.

The pharmaceutical composition may comprise additional active ingredients, such as immuno-stimulating agents, preferably selected from a hematopoietic cell growth factor, a cytokine, an antigenic molecule (or antigen) and an adjuvant, for combined, separate or sequential use.

Such additional active ingredients may be formulated in combination with the IL-7, or, separately, for combined, separate or sequential use. In a first variant, the active ingredients are formulated together, in the same recipient or vessel. In another, preferred variant, they are conditioned separately, i.e., in distinct vessels or recipients. According to this embodiment, the ingredients may be administered separately, e.g., simultaneously or sequentially (e.g., at different injection sites or at different time points), to produce the most efficient biological effect. Also, as mentioned above, repeated administrations of one or the two active ingredients may be performed.

In this respect, the invention relates to a pharmaceutical composition comprising a hyperglycosylated IL-7 composition as described above and an active ingredient selected from an immuno-stimulant and an antigenic molecule, for combined, separate or sequential use. Adjuvants are preferably formulated separately.

The hematopoietic cell growth factor is preferably selected from the Stem Cell Factor (SCF), particularly the soluble form of the SCF, G-CSF, GM-CSF, Flt-3 ligand, IL-15 and IL-2. Typical examples of cytokines or chemokines for vaccine enhancement include cytokines that induce and/or stimulate a Th1-type immune response. The cytokine is preferably selected from α or γ interferon, IL-2, IL-12, RANTES, B7-1, MIP-2 and MIP-1α. It should be understood that other factors such as NK cell activators and/or NKT cell activators, FGF7 or FGF10, interleukins and/or hormones may be used in combination with IL-7 to provide additional therapeutic benefit.

A specific composition of this invention comprises a hyperglycosylated IL-7 composition as described above and Stem Cell Factor, particularly the soluble form thereof, IL-15 and/or Flt-3 ligand and/or FGF10.

Another specific composition of this invention comprises a hyperglycosylated IL-7 composition as described above and a cytokine selected from α or γ interferon, IL-2, IL-12, RANTES and MIP-1α.

Another specific composition of this invention comprises a hyperglycosylated IL-7 composition as described above, a Stem Cell Factor and a cytokine.

As indicated above, the pharmaceutical composition may further comprise one or several antigens (or antigenic molecules), for combined, separate or sequential use. The antigen may be any synthetic or natural peptide, a recombinant protein, a killed, inactivated or attenuated pathogen product, a microorganism, a parasite, a lipid, etc., a portion thereof and a combination thereof. The antigen may be an entire protein, or any epitope-containing fragment or portion thereof, particularly peptides that are presented to the immune system through MHC class I or MHC class II molecules. The antigen can be any viral antigen, bacterial antigen, parasite antigen, tumor antigen, etc. Specific examples of antigens include antigens derived from HIV, Varicella Zoster virus, Influenza virus, Epstein Barr virus, type I or II Herpes Simplex virus, human cytomegalovirus, Dengue virus, Hepatitis A, B, C, D or E virus, Syncytium respiratory virus, human papilloma virus, *mycobacterium tuberculosis, Toxoplasma* and *Chlamydia*.

A particular object of this invention relates to a composition comprising a hyperglycosylated IL-7 composition as described above and an antigenic molecule, for combined, separate or sequential use. The composition may further comprise one or several immuno-stimulating agents as disclosed above, for combined, separate or sequential use.

A further particular object of the present invention concerns a pharmaceutical composition comprising hyperglycosylated IL-7 composition as described above, wherein said pharmaceutical composition is administered simultaneously, a few days before or sequentially with one or several antigenic molecules in order to obtain and/or stimulate an antigen-specific immune response in a subject.

A further particular object of the present invention concerns a method of causing or enhancing an antigen-specific immune response in a subject, comprising administering to a subject said antigen (or an epitope-containing fragment thereof) and a hyperglycosylated IL-7 composition as described above. The composition may be administered simultaneously, a few days before or sequentially with, and more preferably before said antigen in order to obtain and/or stimulate an antigen-specific immune response in a subject.

In another preferred embodiment, the composition of the invention further comprises an adjuvant. The adjuvant may be selected from any substance, mixture, solute or composition facilitating or increasing the immunogenicity of an antigen and able to induce a Th1-type immune response, such as CpG, QS21, ISCOM and monophosphoryl lipid A. Such adjuvants are particularly suited to produce and/or amplify a specific immune response against antigen(s) in mammalian subjects, particularly in humans. The adjuvant is preferably conditioned and administered separately from the IL-7 containing composition and/or at a distinct site of injection, preferably with the desired antigen(s).

The present invention also concerns a pharmaceutical composition comprising an effective amount of a human hyperglycosylated IL-7 composition according to the invention in admixture with a suitable diluent, excipient or carrier, for parenteral administration to a human patient for prophylactic or therapeutic stimulation of B or T lymphocyte development and proliferation, or for augmentation of an immune response. The pharmaceutical compositions of the invention induce a prolonged lymphopoiesis stimulation and/or amplified immune responses.

A pharmaceutical composition according to the invention may also be used in a human patient for prophylactic or therapeutic stimulation of B or T lymphocyte development and proliferation, for enhancement of global and/or specific immuno-reconstitution, or for enhancement of humoral and/or cellular immune responses.

A particular pharmaceutical composition according to the invention is for use to prevent or reduce opportunistic infections in immunodeficient patients.

Another particular pharmaceutical composition according to the invention is for use to prolong lymphopoiesis stimulation and/or to produce specific immune response not only against dominant epitopes but also against sub-dominant or less immunogenic epitopes, epitopes having a lower affinity for the T cell receptor, which will allow to broaden the repertoire of a specific immune response in human patients.

The invention is particularly suited to produce a preventive or curative immune response in subjects, such as immunodeficient patients, cancer patients, patients undergoing grafts, patients infected with a virus or a parasite, elderly patients or any patients having low CD4 count etc.

Specific and preferred uses of the IL-7 polypeptides and compositions of this invention include the use:
- as a vaccine enhancer (administration of said composition before, during or substantially simultaneously with antigen administration) in an amount effective to induce enhancement of specific immune response against malignant cells or infectious agents; and to induce immune reconstitution of patients whatever the origin: infectious, radiations, Transplantations (BMT, SCT) or drugs;

The IL-7 polypeptides and compositions of this invention may be used either alone or in combination with other active ingredients, such as lymphopoietic factors including, without limitation, SCF, Flt3-L, α-lFN, γ-IFN, IL-2, IL-3, IL-4, IL-12, IL-15, IL-18 and/or IL-21. Where combined therapy is used, the various ingredients may be administered simultaneously, separately or sequentially, and may be conditioned together or separately.

The IL-7 polypeptides and compositions of this invention may be used in various areas, including to enhance vaccination in the field of animal health and to minimize the number of active substance administrations.

The invention further provides a method for treating a viral infection, such as HIV infection, viral hepatitis, West Nile fever, Dengue, which method comprises administering to an infected patient, a hyperglycosylated IL-7 polypeptide composition.

In a particular embodiment, the hyperglycosylated IL-7 polypeptide is to be administered in association with an interferon molecule. The interferon molecule can be for instance alpha IFN (leukocyte IFN), beta IFN (fibroblast IFN), gamma IFN (immune IFN), omega IFN or tau IFN (trophoblastic factor).

The invention further provides a method for improving a thymopoietic recovery in immuno-compromised subject, which method comprises administering to an immuno-compromised subject, a hyperglycosylated IL-7 polypeptide composition.

Preferably the hyperglycosylated IL-7 polypeptide is then to be administered in association with a keratinocyte growth factor, a stem cell factor, a gonadostimulin antagonist or a growth hormone.

The hyperglycosyltated IL-7 polypeptide can also be used in a method for providing a therapeutic immunization against malignant cells, virus or bacteria, wherein the hyperglycosylated IL-7 polypeptide is to be administered in association with an antigen or a mixture of antigens, e.g. those described above. In this situation, the hyperglycosylated IL-7 polypeptide may be further administered in association with GM-CSF.

A further object of this invention is a method for ex-vivo enhancing expansion of T cells, which method comprises contacting T cells with a hyperglycosylated IL-7 polypeptide or composition, hereby enhancing expansion of the T cells. This method is particularly useful to prepare T cells suitable for treating patients with cancer or viral infection by adoptive immunotherapy. Adoptive immunotherapy is an ex vivo methodology for selective expansion of specific T cells targeting specific antigens (malignant or viral). This immunotherapeutic technique generally includes isolation of Ag-specific T lymphocytes from whole blood of the patient, ex vivo expansion of theses T cells using IL-7 polypeptides, optionally ex vivo activation of theses T cells by other cytokines and administration to the patient. Other techniques are possible. IL-7 polypeptides improve survival of these T cell populations which further show an enhanced cytotoxic activity.

Production Methods and Tools

Another aspect of the present invention is to provide appropriate constructs and methods for producing the above compositions, particularly the above hyperglycosylated IL-7 polypeptides, compositions and drug substances, in sufficient quantities and quality for pharmaceutical use thereof.

In particular, as discussed above, the present invention provides vectors as well as recombinant host cells that may be used to produce recombinant human IL-7 polypeptides of this invention in various competent host cells, as well as for gene therapy purposes.

The vector may be a plasmid, virus, phage, cosmid, episome, etc. Preferred vectors are viral vectors (e.g., recombinant adenoviruses) and plasmids, which can be produced based on commercially available backbones, such as pBR, pcDNA, pUC, pET, pVITRO, etc. The vector typically comprises regulatory elements or sequences to control or mediate expression of an IL-7 polypeptide. The regulatory sequences may be chosen from promoters, enhancers, silencers, tissue-specific signals, peptide signals, introns, terminators, polyA sequences, GC regions, etc., or a combination thereof. Such regulatory elements or sequences may be derived from mammalian, fungal, plant, bacterial, yeast, bacteriophage or viral genes, or from artificial sources. Useful promoters for prokaryote expression (such as E. coli) include T7 RNA polymerase promoter (pT7), TAC promoter (pTAC), Trp promoter, Lac promoter, Tre promoter, PhoA promoter for example. Suitable promoters for expression in mammalian cells include viral promoters (e.g., CMV, LTR, RSV, SV40, TK, pCAG, etc.), domestic gene promoters (e.g., E1fα, chicken Pactine, Ubiquitine, INSM1, etc.), hybrid promoters (e.g., actine/globin, etc.), etc. A vector may comprise more than one promoter. The promoters may be inducible or regulated. For instance, the use of inducible or regulated promoters allows a better control of production by dissociating the culture from production phases. Inducible or regulated promoters may be found in the literature, such as the Tetracycline system, the Geneswitch system, the Ecdysone system, the Oestradiol system, the RU486 system, the Cumate system, the methallothioneine promoter etc. Other systems are based on electric currents or microwaves, such as focalized ultrasound system, AIR induced expression system and the like. These systems can be used to control expression of an IL-7 polypeptide according to the invention.

The IL-7 may be co-expressed with an anti-apoptotic factor (e.g., iex, Bcl2, BclXL, etc.) or cycline (e.i. p21, p27, etc.). The cDNAs coding for said IL-7 and for said anti-apoptotic factor may be both placed downstream of the same promoter, but separated by an IRES sequence, or each of them downstream of its own promoter.

The vector may further comprise an origin of replication and/or a marker gene, which may be selected from conventional sequences. An amplification selection marker such as the DHFR gene can be inserted in the backbone of the vector.

The vector may further comprise various combinations of these different elements which may be organized in different ways.

The present invention also provides recombinant host cells comprising a nucleic acid or a vector as described above. The host cell may be selected from any eukaryotic and prokaryotic cells, typically from a mammalian cell (in particular a human, rodent, canine cell), a bacterial cell (in particular E. coli, Bacillus Brevis, Bacillus subtilis), a yeast cell, a plant cell and an insect cell. These host cells may be adapted to serum-free media. Production may also be accomplished in a transgenic animal or plant.

Preferred recombinant host cells are selected from mammalian cells, in particular human cells as well as derivatives or mutants thereof.

Specific examples of suitable host cells include Chinese Hamster Ovary (CHO) cells, Baby Hamster Kidney (BHK) cells, Human Embryonic Kidney (HEK-293) cells, human epidermal keratinocytes (HEK), human stromal or epithelial cells, PERC6, etc. In such mammalian cells, IL-7 may be produced as a secreted protein using functional signal peptide sequences.

A specific object of this invention is a eukaryotic host cell comprising a nucleic acid molecule comprising SEQ ID NO: 2, 4 or 6.

A further object of the present invention relates to antibodies immunoreactive with an IL-7 composition or polypeptide as described above. Such antibodies may be produced according to conventional methods, including immunization of animals and collecting the serum (polyclonal) or preparing hybridomas from spleen cells (monoclonal). Fragments (e.g., Fab') or engineered derivatives of antibodies (e.g., ScFv or diabodies or minibodies) may be produced by known biological and chemical methods. Preferred antibodies are specifically immunoreactive with a hyperglycosylated IL-7 polypeptide as described above, i.e., can bind the hyperglycosylated IL-7 polypeptide without substantially binding un- or mono-glycosylated polypeptides. Although non-specific or less effective binding to such other antigens may be observed, such non-specific binding can be distinguished from specific binding to the particular hyperglycosylated IL-7 polypeptides of this invention.

The antibody is preferably of simian, murine or human origin or has been humanized.

The invention also relates to a hybridoma cell line that produces a monoclonal antibody as described above.

Such antibodies are useful in detecting hyperglycosylated IL-7 polypeptide or in neutralizing IL-7 biological activity in assays or experiments involving multiple lymphokines. A composition suitable for diagnosis, assay or therapy comprising such monoclonal antibodies is also an object of the present invention.

Another object of the present invention relates to processes which can be used, on an industrial scale, for the production of a pharmaceutical grade, substantially pure hyperglycosylated IL-7 polypeptide as described above. The process leads to high yields of recombinant IL-7 conformer suitable for therapeutic use. The invention also provides novel methods of controlling IL-7-containing compositions, to determine the presence of amount of hyperglycosylated IL-7 polypeptide as described above.

In a particular aspect, the method of producing hyperglycosylated IL-7 polypeptides or compositions as defined above comprises:
a) culturing a recombinant host cell as described above, and
b) collecting an IL-7 polypeptide produced from said cells.

The sample may be subjected to various treatments or conditions in order to increase purity of IL-7, to remove cell debris or viral particles, etc. Typical examples of such treatments include centrifugation, clarification and/or dia-ultra-nano-filtration. The sample may thus be enriched for IL-7 polypeptide.

To increase the yields or efficiency of the method, it is highly desirable to produce a sample containing or enriched in correctly folded and glycosylated IL-7 polypeptides.

The hyperglycosylated IL-7 polypeptide may be purified by different techniques known per se, but which have not been used so far in the present combination to produce a hyperglycosylated IL-7 polypeptide. These techniques are more preferably selected from hydrophobic interaction chromatography, ion exchange chromatography, affinity chromatography and gel filtration chromatography, either alone or in various combinations. Such methods allow removal of host cell DNA and other impurities which would lower recovery. In a preferred embodiment, step ii) comprises a hydrophobic interaction chromatography step. Such chromatography may be carried out using various supports and formats, preferably using HIC butyl. Step ii) may be carried out on any support, preferably on batch or in column using an appropriate gel.

In a preferred embodiment, the purification step comprises loading the sample through a column packed with a specific gel (Sephadex for example).

In another preferred embodiment, the purification step comprises a polishing step involving loading the sample through a column packed with a specific gel (Source 15S) to concentrate recovered protein of interest and eliminate possible residual protein contaminants.

In another particular embodiment the purifying step comprises loading the sample through a column packed with a specific gel comprising a monoclonal anti IL-7 antibody immobilized on a resin (dextran sulfate or heparin for example).

These methods allow the reproducible and efficient production of a substantially pure hyperglycosylated IL-7 polypeptide as described above. The methods are particularly advantageous since the recombinant IL-7 can be obtained with a purity of at least 95% by weight, preferably at least 98% by weight and even more preferably at least 99% or even 99.5% by weight with respect to the total amount of IL-7.

Each step of the above described process may be controlled by analytical methods, including SDS-PAGE analysis. The primary structure of the optimized IL-7 may be controlled and characterized by determining the gene and/or amino acid sequence, by peptide mapping analysis, after trypsic digestion, by determining molecular weight with SDS PAGE, size exclusion HPLC, Mass spectrometry such as MALDI TOF or electrospray or the like, by determining hydrophobicity with reverse phase HPLC for example, and/or by determining the electric charge with cation exchange chromatography HPLC or isoelectrofocalisation analysis for example.

A further embodiment of the invention relates to IL-7 production methods as described above, wherein IL-7 expression by the recombinant host cells is inducible, regulated or transient, so that the cell culture and IL-7 expression phases can be dissociated. More particularly, in a particular embodiment, IL-7 expression can be repressed or minimized during recombinant cell growth, expansion and/or culturing, to allow the production of large amounts of recombinant host cells without any IL-7-mediated potential toxic effect. Then, IL-7 expression can be induced within the cell culture (or on a sample thereof), allowing the efficient synthesis and release of recombinant IL-7.

An object of this invention thus also resides in a method of producing a recombinant IL-7 polypeptide, comprising culturing a recombinant host cell as disclosed above comprising a nucleic acid molecule encoding said IL-7 polypeptide and recovering the recombinant IL-7 polypeptide produced, wherein said nucleic acid molecule provides for a regulated or inducible expression of said IL-7 polypeptide, so that expression of said IL-7 polypeptide can be repressed or minimized during recombinant cell growth and induced during production phase. The nucleic acid typically comprises an inducible promoter, which can be repressed or activated in the presence or absence of a specific agent contained or added into the culture media. The method is particularly suited to produce an IL-7 hyperglycosylated conformer as disclosed above.

Various regulated or inducible expression systems have been disclosed in the art, which are functional in mammalian host cells and can be used in the present invention. These include the Tetracycline TetOn/Off system, Geneswitch system (Invitrogen) with Mifepristone as inducible agent and GAL4-E1b promoter, Ecdysone system (induction with ponasterone A or muristerone A, analogs of insect steroid hormones)(Invitrogen), methallothioneine promoter (inducible by zinc), Oestradiol system, RU486 system, focalized ultrasound system, AIR (Acetaldehyde inducible regulation) induced expression system, Cumate system (Q-mate; Qbiogen), Cre-Lox system, etc. These regulated or inducible expression systems may be used in various cells, such as for instance HEK293, HEK293 EBNA, HEK, T-REX™-293, T-REX™-HeLa, T-REX™-CHO or T-REX™-Jurkat cell lines, transformed with a recombinant vector designed to express recombinant IL-7 after induction.

Alternatively, transient transfection can be used to dissociate cell expansion from IL-7 production. In this regard, efficient gene delivery vectors are used to introduce an IL-7 coding sequence into cells upon expansion thereof. More preferably, the vector system for transient transfection is a viral vector, such as a recombinant adenovirus or an episomal vector [e.g., pCEPH (Invitrogene), pTT (IRB: Durocher Y. et al. Nucl. Acids. Res., 2002, 30(2)) or using MAR sequences]. Adenoviruses (and other viral vectors such as AAVs, for instance), can be produced according to techniques known in the art. Typically, E1-defective adenoviruses are produced in a E1-complementing cell line, such as HEK293, PERC6 cells, etc. Such transient transfection process can be implemented in various mammalian cells in culture, such as A549-, HeLa—, VERO—, BHK— or CHO— transformed cells for example (as disclosed in example A4). An alternative transient expression method suitable for use in the present invention is disclosed for instance in the next article: Durocher Y. et al. Nucl. Acids. Res., 2002, 30(2) in HEK293 EBNA or HEK293 cells.

In a preferred embodiment, the production methods of this invention comprise an additional step c) of characterizing and measuring or quantifying the particular hyperglycosylated IL-7 polypeptide as disclosed above contained in the resulting product. The physical and biological characterization of the desired hyperglycosylated IL-7 polypeptide may be obtained by Mass spectrometry (MALDI-TOF or electrospray), infrared spectroscopy, nuclear magnetic resonance (NMR), by determining circular dichroïsm, by assessment of the biological activity of the IL-7 in a specific bioassay, by measuring the affinity towards a specific monoclonal antibody raised against said hyperglycosylated IL-7 polypeptide, or heparin affinity HPLC. Once characterized, the quantification of said conformer may be performed by ELISA, bioassay, affinity of said hyperglycosylated IL-7 polypeptide for IL-7 receptor and any method of protein quantification if applied to the isolated conformer.

In this regard, the invention also provides and concerns a method to identify and/or measure the quantity of hyperglycosylated IL-7 polypeptide and/or related impurities in a sample, particularly in a pharmaceutical preparation. Such characterization methods can be used to initially characterize and qualify the protein for filing a therapeutic use, in quality control of pharmaceutical batches. The invention proposes, for the first time, a method of characterizing and controlling IL-7-containing preparations, to determine the presence and/or relative quantity of hyperglycosylated IL-7 polypeptide of this invention. Preferred methods use Bicinchoninic Acid (BCA) protein Assay, SDS-PAGE, western blot, size-exclusion HPLC, reverse phase HPLC, ion exchange HPLC, hydrophobic interaction HPLC, Amino Acid Assay (AAA), Isoelectrofocalisation (IEF), ELISA, UV absorption and/or a Bioassay. These methods may be carried out alone or in various combinations.

The invention also provides a method of producing an IL-7 drug substance or pharmaceutical composition, said method comprising (i) culturing a recombinant host cell encoding an IL-7 polypeptide, (ii) isolating said recombinant polypeptide to produce an IL-7 drug substance and (iii) conditioning said IL-7 drug substance to produce a pharmaceutical composition suitable for therapeutic or vaccine use, said method further comprising a step of identifying, characterizing or measuring, in said drug substance or pharmaceutical composition, the quantity and/or quality of hyperglycosylated IL-7 polypeptide as defined above and, more preferably, a step of selecting the drug substance or pharmaceutical composition which comprises, as the active ingredient, more than about 90%, preferably 95%, more preferably 98% of said hyperglycosylated IL-7 polypeptide.

The characterizing step may be carried out by a variety of techniques, more preferably by mass spectrometry-related methods, with or without trypsic digest, Lectine Affinity Chromatography, Amini Acid Assay (AAA), Endo- and Exo- N- and O-glycanase digestions (PNGase A/F, O-glycosidase, neuraminidase), Fluorophore Assisted Carbohydrate Electrophoresis, MALDI TOF or Electrospray Mass Spectrometry, specific monoclonal antibody analysis for disulfide bridges and/or conformation characterization. The identification of molecular variants and product-related impurities is preferably performed by using one or several methods selected from bi-dimensional electrophoresis, isoelectric focusing and ion-exchange chromatography for deamidated forms, size exclusion chromatography and SDS-PAGE analysis for multimeric forms, and HPLC reverse phase with or without enzymatic predigestion for truncated forms.

The step is particularly suited for quality control of clinical or pharmaceutical compositions, whereby only compositions comprising more than about 95% of the above hyperglycosylated IL-7 polypeptide are retained, preferably more than about 96%, 98% or 99.5%. All these hyperglycosylated IL-7 polypeptide showing an average isoelectric point below 6.5.

Another object of the present invention relates to the use of a recombinant hyperglycosylated IL-7 polypeptide obtained with the processes as described above, for the manufacture of a pharmaceutical composition to prevent or treat a disease associated with an immunodeficiency, particularly to induce a prolonged lymphopoiesis stimulation, to cause and/or amplify an immune response, particularly an antigen-specific immune response.

A further object of the invention relates to the use of a hyperglycosylated IL-7 polypeptide as a tool for experimental and pharmacological use in mammalians for veterinary applications.

Other aspects and advantages of the present invention will be described in the following examples, which should be regarded as illustrative and not limiting the scope of the present application.

EXAMPLES

Example A

Construction and Expression of Optimized Human (h) and Simian (s) IL-7-Coding Nucleotide Sequences in Mammalian Cells A1. Construction of an Optimized Human IL-7-Coding Nucleotide Sequence:

1.1. Peptide Signal Optimization:

As the expression of IL-7 cDNA fragments linked at the 5' end to the natural IL-7 peptide signal was very low, we tested several signal peptide sequences.

The new human IL-7 encoding cDNA sequences were chemically obtained from assembled synthetic oligonucleotides.

Several signal peptide sequences were tested: signal peptide (SP) of highly secreted proteins (Barash et al.; 2002; Biochemical and Biophysical Research Communications 294:835-842):

IL-7 SP

MFHVSFRYIF GLPPLILVLL PVASS (SEQ ID NO: 13)

EPO SP

MGVHECPAWL WLLLSLLSLP LGLPVLG (SEQ ID NO: 14)

SEAP SP

MLLLLLLLGL RLQLSLG (SEQ ID NO: 15)

IgGkappa SP

METDTLLLWV LLLWVPGSTG (SEQ ID NO: 16)

Lactotransferin/vitronectin SP

MKLVFLVLLF LGALGVALA (SEQ ID NO: 17)

Cystatin bis SP

MARPLCTLLL LMATLAVALA (SEQ ID NO: 18)

EPO/IL-7 a new hydrid SP

MGVHECPAWL WLLLSLLSLV LLPVAS (SEQ ID NO: 19)

The obtained cDNAs sequences were inserted into the pTT5 vector (Durocher et al.; 2002; Nucl. Ac. Res.; 30) for transient expression in mammalian cells such as HEK293 cells, CHO cells.

To check for the good cleavage of the signal peptide, the N terminal amino acid was determined for each obtained protein; hIL-7 integrity was maintained. Cystatin, IgG, EPO and the hybrid EP/7 appeared as the best signal peptide sequences. Indeed, hIL-7 expression is enhanced by, at least, a factor 10.

1.2. Human IL-7-Coding Nucleotide Sequence Optimization:

Maintaining the EP/7hIL-7 amino acid sequence, the nucleic acid sequence was optimized by elimination of human rare codons (using Graphical Codon Usage Analyser software)

enhancing mRNA stability by enhancing "GC" content of the sequence, except for the signal peptide sequence (Kim et al.; 1997; Gene; 199), and minimizing succession of "CA" dinucleotides.

The sequence is depicted in SEQ ID NO: 2.

A2. Construction of an Optimized Simian IL-7-Coding Nucleotide Sequence:

As described for the human IL-7-coding sequence, an EP/7-sIL-7 optimized sequence was synthesized (SEQ ID NO: 3).

A3. Construction of Canine IL-7-Coding Nucleotide Sequence:

Canine IL-7 cDNA was amplified by PCR from a dog kidney cDNA library (Biochain), cloned and sequenced as described above for the human IL-7-coding sequence, an IL-7SP or EP/7SP-cIL-7 sequence was synthesized (SEQ ID NO: 6).

A4. Mammalian Expression (BHK Cell Expression, or CHO Cell Expression or HEK-293 Cell Expression):

The IL-7 encoding cDNA sequences were amplificated by polymerase chain reaction (PCR)(Mullis et al.; 1987; Methods in Enzymology; 155:335-350) to create the restriction sites (NotI/SwaI) for cloning into the expression vector.

The expression system ph-pgk.EP7-hIL-7 (FIG. 1) or pBh-pgk.EP7-hIL-7 (FIG. 2) was designed to express an IL-7 protein predicted from the translation of the natural human IL-7 gene sequence. Selection for recombinant vector-containing cells was doned on the basis of the antibiotic (Ampicilin for cloning in *E. coli* and hygromycin for expression in mammalian cells) resistance marker genes carried on the vector.

This expression vector has been entirely constructed at CYTHERIS, beginning from pIC20H plasmid (ATCC) conferring ampicillin resistance to the system. It contains 2 mammalian production units:

1/one for the expression of the IL-7 encoding sequences, under the control of the pgk promoter, and a synthetic polyA sequence avoiding transcription through the pgk promoter.

2/one for the expression of the hygromycin resistance, under the control of the "sv40 enhancer—tk promoter".

Following sequences were inserted into this preliminary vector:

"hph-ef1a pA": HindIII/SbfI fragment from pVitro2.mcs (Invitrogen);

tk promoter: EcoRI/HindIII PCR fragment from pMEP4 (Invitrogen);

sv40 enhancer: BssHII/EcoRI PCR fragment from pVitro2.mcs (Invitrogen);

MAR rabbit βglobin: a putative "Matrix Attachment Region" for a better integration in highly transcribed region of the chromatin, EcoRV/AgeI rabbit βglobin intron2 PCR fragment from pSG5 (Stratagene);

SpA: StuI/BspEI fragment from pCAT3 control (Promega)

Pgk promoter: KpnI/BssHII PCR fragment from pQBI.pgk (Q-biogen);

5'UTRint1: HindIII chimeric intron fragment from pCAT3-control (Promega);

NotI/SwaI or NotI/Pm/I IL-7 encoding cDNA and mutants;

hghpA: NruI/SwaI synthetic synthesis from human growth hormone cDNA sequence described by M. Goodman (DeNoto et al.; 1981; Nucl. Acid. Res.; 9 (51):3719-3730).

Some variants of the vector were prepared with other IL-7 promoter than the pgk promoter: Ef1alpha, snRNA Ul, actin, Ubiquitin, CMV promoters, etc, or other selection marker: neomycine, etc.

The mammalian (HEK-293, CHO or BHK) expression vector comprising SEQ ID NO: 2, is called ph-pgk.EP7-hIL-7 or pBh-pgk.EP7-hIL-7. Stable Expression of human IL-7 in HEK-293 or CHO transfected cells was achieved using the expression vector ph-pgk.EP7-hIL-7 or pBh-pgk.EP7-hIL-7. After linearization by NdeI, expression vector, ph-pgk.EP7-hIL-7 or pBh-pgk.EP7-hIL-7, was transfected in the mammalian host cells using methods known to those skilled in the art. The selectable marker used to establish stable transformants was hygromycin (Invitrogen).

A5. Inducible Mammalian Expression (Methalothioneine Promoter "MT1"):

In the same expression vector, pgk promoter has also been replaced by a chemically synthesized BspEI/BssHII "*Mus*

*musculus* MT1" sequence, as referred in PubMed(No X53530)(Carter et al.; 1984; Proc. Natl. Acad. Sci. USA; 81:7392-7396).

MT1 is a metal-dependent transcription factor promoter. Expression of stable clones is then zinc dependent.

A6. Mammalian Co-Expression of IL-7 and Bcl2 or BclXL (BHK Cell Expression, or CHO Cell Expression or HEK-293 Cell Expression):

In order to enhance cell viability in mammalian host cell culture and therefore to optimize the amounts of IL-7 production, a variant expression plasmid was prepared by inserting Bcl2 cDNA sequence in between tk promoter and hph cDNA so that anti apoptotic action of Bcl2 could be tested in bioreactor production (Zhong et al.; 1993; Proc. Natl. Acad. Sci. USA; 90:4533-4537—Lee et al.; 2000; Journal of cell Science; 114(4):677-684). (See FIG. 2).

Example B

Construction and Expression of Hyperglycosylated Analogs of IL-7-Coding Nucleotide Sequences in Mammalian Cells B1. Construction of cDNA Sequences of Hyperglycosylated IL-7 Analogs The hyperglycosylated IL-7 analogs were obtained using several techniques including mutagenesis methods. Hyperglycosylated IL-7 analogs (alternatively: HG37-40-104-126 and -147) were chemically constructed from assembled synthetic oligonucleotides. Several analogs were obtained by introducing one or more desired mutations so that giving IL-7 analogs having one or more additional glycosylation sites. Thus the resulting full length cDNA sequence containing one or multiple desired additional glycosylation sites were inserted, after digestion with NotI and PmlI restriction enzymes, in between the NotI/PmI restriction sites for direct cloning into the expression vector (similar to FIG. 1 or 2 but containing appropriate IL-7 sequence).

B2. Expression of cDNA Sequences of Hyperglycosylated IL-7 Analogs

The expression of hyperglycosylated IL-7 analogs was conducted as described above in sections A4 to A6.

Example C

Production of Recombinant hIL-7 in Bioreactor Culture Conditions

The best stable positive clone, as in example A4 was adapted to serum-free suspension culture by several media and components screenings in order to produce a clone optimized for productivity and growth in high cell density culture. Before seeding the 100 to 2000 L bioreactor, pre-cultures are performed in the "wave bag" system. Cell culture is performed in a 100 to 2000 liters bioreactor with a perfusion system or a fed-batch system during 10 to 15 days. Cells were amplified to a concentration of 10 millions cells/ml in a low-glutamine content medium supplemented with plant peptones.

In a first expansion step the culture temperature is regulated at 37° C. to increase cell density. After a few days, the temperature was lowered at around 28/32° C. to inhibit cell growth and allow a better expression level. Moreover, decreasing temperature decreases the speed of the secretion pathway, favoring better glycosylation of the expressed IL-7 with increased site occupancy.

A few days before the end of the culture, IL-7 expression was boosted by addition of 0.5-10 mM Sodium Butyrate in the medium.

Figure 3:
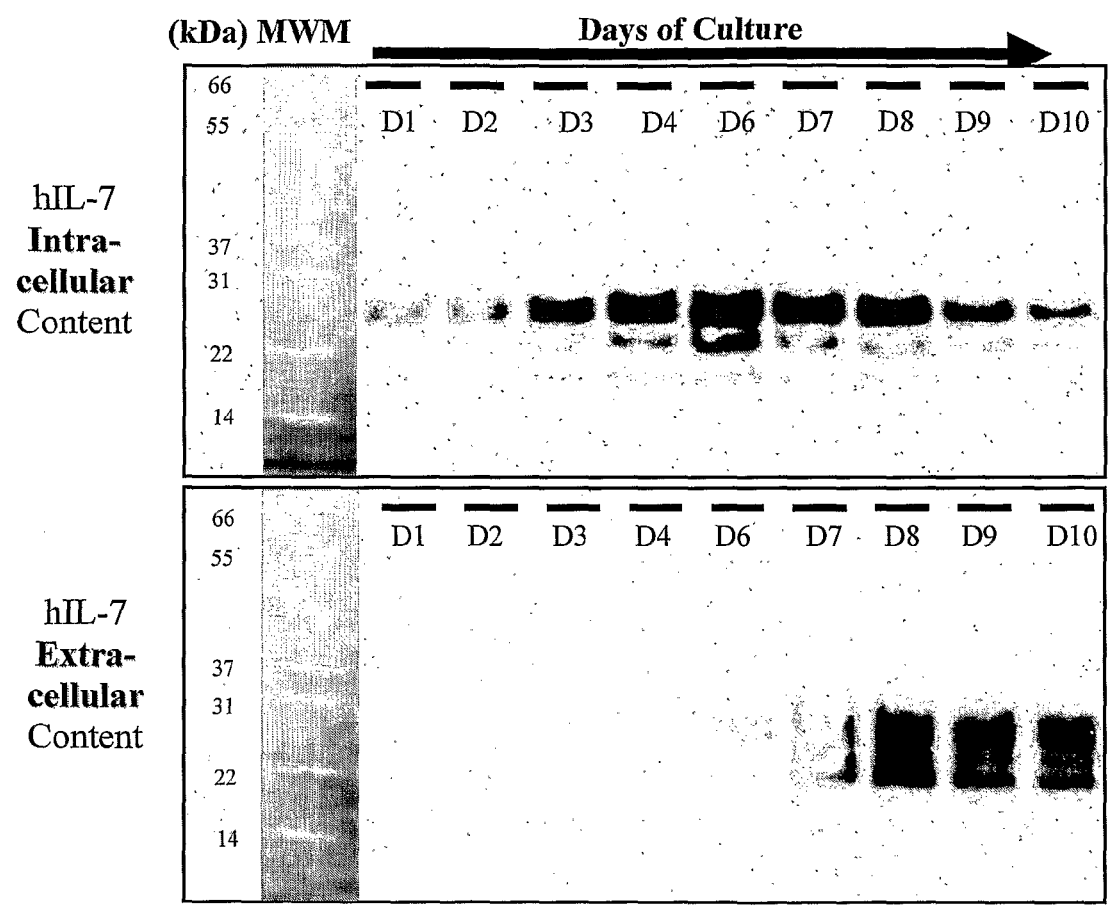

Under conditions described above, IL-7 expression was monitored both inside the cells and in the culture medium (FIG. 3).

To produce high MW IL7 glycoforms, 3 g/L glucose and 3 mM glutamine are maintained in the medium during the culture as well as a good oxygenation. One also monitors the amino acids consumption and feeds the culture with depleted amino acids. Cell culture is harvested as soon as cell viability decreases below 90%.

Example D

Purification of Recombinant Human IL-7 Product Expressed in HEK-293 and CHO Cells Crude cell culture medium was collected and centrifuged to pellet whole cells and cells debris. Alternatively this can be achieved by in depth filtration on clarification capsules or modules such as Mustang XT capsule (Pall), Sartoclear P (Sartorius), Millistak+Opticap (Millipore) or hollow fiber cartridges (AXH cross flow 10 (GE)) or equivalent. Centrifuged culture medium was concentrated approximately 10-fold with Centrasette Cassette apparatus, membrane cut off 10 kDa (Pall Life Sciences) to reduce the volume of supernatant. Any other filtration/concentration system with similar porosity could also be used.

The concentrated supernatant was centrifuged, adjusted to pH 7.5 and applied to a Q Sepharose Fast Flow (General Electric Healthcare) column equilibrated with 50 mM sodium phosphate pH 7.5. The protein was then recovered in the flow through. During this negative chromatographic step, various contaminants among which DNA were eliminated. An alternative to this step was to use validated Mustang Q membrane cassettes (Pall) in similar conditions, for better yield and/or slightly faster process. Another alternative to this step is to capture the protein on a strong Anion exchanger resin (Q Ceramic Hyper D (Biosepra), Capto Q (GE)) or membrane (Sartobind Q, Sartorius).

After this prepurification step, a capture step was performed on a strong cation exchanger resin. The flow through collected at the end of previous step was loaded onto a Fractogel EMD SO3$^-$ (Merck) column equilibrated with loading buffer (50 mM sodium phosphate pH 7.5), and washed with 50 mM sodium phosphate pH 7.5. Elution was carried out using a linear NaCl gradient (15 column volumes) in 50 mM sodium phosphate pH 7.5.

Active fractions were pooled and inactivated during 30 minutes at pH 3.5 at room temperature to eliminate virus. An alternative to this process is to replace this viral inactivation step by a multilayer nanofiltration at the end of the process. After viral inactivation, pooled protein fractions were diluted 2-fold in buffer (200 mM sodium phosphate pH 7, 3M ammonium sulphate) and pH was adjusted to 7. Then, the protein solution was loaded onto a Hydrophobic Interaction Chromatography (HIC) Butyl Toyopearl 650-M (Tosoh) column equilibrated with the loading buffer (50 mM sodium phosphate pH 7+1.5M ammonium sulphate). After washing with the loading buffer, IL-7 was eluted with 25 column volumes of a salt gradient ranging from 1.5 M to 0 M ammonium sulphate in 50 mM sodium phosphate pH 7.

Alternative HIC resin such as hexyl Toyopearl 650-M (Tosoh), Butyl/Octyl Sepharose™ 4 Fast Flow (General Electric Healthcare), can be utilized for this step, Another alternative to HIC for scaling up purposes was to use another matrix such as MEP HyperCel (Pall Biosepra) for similar results.

The combination of the above-mentioned capture step and Hydrophobic Interaction Chromatography allowed optimal separation of the different glycosylated IL-7 isoforms (from B1 to B10 as indicated on FIG. 4), according to their intrinsic physico-chemical properties. Adequate selection of elution fractions (fraction from B1 to B4) lead to an enrichment in the 3N- associated or not to 1O-glycosylated hIL-7 entity. An example of such glycoform separation is shown in FIG. 4.

The highly glycosylated IL-7 fractions were pooled and loaded onto a G25 Sephadex (General Electric Healthcare) column equilibrated with low salt buffer (20 mM sodium acetate pH 6). An alternative to this step is to diafiltrate the high salt protein pool using 5 or 10 KDa molecular weight cut off TFF membranes (Qvick start membranes, (GE), Centramate TFF (PaII)).

The protein fractions obtained from G25 step were loaded onto a Source 15S (General Electric Healthcare) column equilibrated with the loading buffer (20 mM acetate sodium pH 6). This polishing step resulted in protein concentration and elimination of the residual contaminants.

The column was washed with sodium acetate loading buffer and the IL-7 protein was eluted with 15 column volumes of a salt gradient ranging from 0 to 1 M NaCl in 20 mM sodium acetate pH 6. Eluted fractions were separated by SDS-PAGE and stained with either Coomassie blue or silver Nitrate. Only the fractions containing IL-7 were pooled to release the final purified IL-7 protein batch.

If viral inactivation has not been conducted before, purification process may also include an additional combination of two filtrations to guaranty optimal viral clearance. Viral removal can be achieved by filtration using a prefiltration device (Planova 75, Asahi Kasei Medical) followed by a nanoporous cellulose membranes (Planova 20N, Asahi Kasei Medical) or by other viral removal membranes (Virosart, Sartorius; DV20, Millipore).

SDS PAGE of the purified *E. coli*, glycosylated and hyperglosylated hIL-7 are shown on FIG. 5.

Shifts in the gel illustrate the level of glycosylation of the protein. Indeed, the hyperglycosylated forms tested here (HG-37-147 and HG-40-104) have a higher molecular weight than the full glycosylated hIL-7.

Example E

Analysis of Glycoprotein Carbohydrates

Production of recombinant human IL-7 was conducted in a CHO cell-based expression system for, but not limited to, the following reasons. CHO cells are the current most validated and most common host used for the production of recombinant human therapeutic glycoprotein. Furthermore, a large set of detailed work reported that CHO cells, including genetically modified CHO cell lines expressing sialyl-α-1-6 transferase, were able to glycosylate recombinant proteins in a manner qualitatively similar to that observed in human cells. This particular feature was of major importance to reduce the potential immunogenicity of the recombinant glycoprotein when injected to human patients.

Purified recombinant human IL-7 product or fractions enriched for particular glycoforms (3N or 3N+2N, associated or not to 1 O-glycan moiety) obtained from transfected CHO cells were analysed by western blot to confirm glycosylation status in comparison to *E. coli*-derived recombinant human IL-7.

The different glycoforms of the CHO-produced and purified IL-7 were differentially characterized using PolyAcrilamide Gel Electrophoresis. Apparent molecular weight glycoprotein entities were ranging between 20 KDa and 35 KDa with a major band at around 27 KDa (observed in SDS-PAGE, see FIG. 5 and FIG. 6), most probably corresponding to a three N-glycosylated form comprising or not one O-glycan moiety. This aspect was specifically addressed by enzymatic deglycosylation of the purified product (FIG. 7).

These glycoforms (3N or 3N+2N, associated or not to 1 O-glycan moiety) of the CHO-produced and purified IL-7 were differentially characterized using mass spectrometry, giving molecular mass superior to 25 KDa for the 3N-glycoform associated or not to 1 O-glycan moiety and superior to 23 KDa for the 2N-glycoform associated or not to 1 O-glycan moiety (see FIG. 8).

Furthermore, the above glycosylated forms present an average isoelectric point of 5.8 reflecting a high sialylation profile (see FIG. 9).

As a comparison, similar analysis with unglycosylated *E. coli*-derived hIL-7 gave a protein with an apparent molecular weight at approximately 18 KDa, and mammalian cells derived hyperglycosylated hIL-7 were exhibiting apparent molecular weight comprised between 27 and 37 KDa General glycosylation complexity and total N-glycan heterogeneity of the purified CHO-derived hIL-7 was assessed by total enzymatic de-glycosylation followed by chromatography separation and mass spectrometry analyses of the generated oligosaccharides.

Purified glycosylated h-IL-7 samples were enzymatically digested with an endoglycosidase such as peptide-N-glycosidase F (PNGaseF, Roche). Released N-linked oligosaccharides were separated from the peptide structure and sorted using a graphite Carbograph 200-300 μl column (Alltech), followed by MALDI-TOF Mass Spectrometry (Voyager Spec, Applied Biosystems). The m/z values corresponding to each peack of the MS spectrum allowed identification of the N-Glycan general structure of the whole hIL-7 molecule.

For specific detection of the sialic acid containing glycans, a carboxymethylation of the PNGase-generated oligosaccharides (as reported in Powell A K & Harvey D J, Rap. Com. Mass Spec. 1996) was undertaken prior to Mass spectrometry analysis.

Analysis of the spectrum generated from purified CHO-derived hIL-7 revealed N-glycans masses ranging from 1340 Da up to 3516 Da. (See FIG. 10).

From the spectrum, the following glycan structure could be determined (see Table 3):

TABLE 3

| m/z Signal | Assignment of observed molecular ions |
|---|---|
| 1338 | $Hex_3HexNAc_4 + Na^+$ |
| 1448 | $Hex_4(dHex)HexNAc_4 + Na^+$ |
| 1485 | $Hex_3(dHex)HexNAc_4 + Na^+$ |
| 1647 | $Hex_4(dHex)HexNAc_4 + Na^+$ |
| 1809 | $Hex_5(dHex)HexNAc_4 + Na^+$ |
| 1824 | $Hex_3(dHex_2)HexNAc_5 + Na^+$ |
| 1970 | $Hex_5(dHex)HexNAc_4(Sulph)_2 + 2Na^+$ |
| 2012 | $Hex_5(dHex)HexNAc_5 + Na^+$ |
| 2157 | $NeuAcCarboxyHex_4(dHex)HexNAc_5 + Na^+$ |
| 2182 | $NeuAcHex_5(dHex)HexNAc_4Sulph + Na^+$ |
| 2318 | $NeuAcCarboxyHex_5(dHex)HexNAc_5 + Na^+$ |
| 2421 | $Hex_3(dHex)HexNAc_8(Sulph) + Na^+$ |
| 2536 | $NeuAcCarboxyHex_6HexNAc_6 + Na^+$ |

TABLE 3-continued

| m/z Signal | Assignment of observed molecular ions |
|---|---|
| 2624 | NeuAc2CarboxyHex$_5$(dHex)HexNAc$_5$ + Na$^+$ |
| 2786 | NeuAc2CarboxyHex$_6$(dHex)HexNAc$_5$ + Na$^+$ |
| 2843 | NeuAc2CarboxyHex$_6$HexNAc$_6$ + Na$^+$ |
| 3092 | NeuAc3CarboxyHex$_6$(dHex)HexNAc$_5$ + Na$^+$ |
| 3153 | NeuAc3CarboxyHex$_6$HexNAc$_6$ + Na$^+$ |

Hex: hexose (Galactose or Mannose), HexNAc: N-acetyl-hexosamine (N-acetyl Glucosamine or N-acetyl Galactosamine), dHex: deoxyhexose (Fucose), Sulph: Sulfate group, NeuAc: N-acetyl neuraminic acid Taking into account i) the respective masses of the observed oligosaccharide moieties, ii) the mass of each monosaccharide and iii) laws of glycan biosynthesis pathways as they are known today, the following highly complex N-glycan structures can be assumed with good probability.

TABLE 4

Complex bi and triantennary mammalian N-glycans characterized on CHO-derived hIL-7(but not limited to):

2420

2477

2536

2623

2785

2843

3092

3149

○ Mannose
□ N-acetylglucosamine
● Galactose
◇ α1-3-Fucose
△ Sialic Acid

Glycosylation complexity was also assessed via determination of molar ratio of the different monosaccharides found on all the glycans (N- and O-glycan if applicable) of the purified CHO-derived hIL-7.

All the glycans of purified glycosylated h-IL-7 samples were chemically treated by methanolysis reaction so as to hydrolyze all the glycosidic links between sugars. Released monosaccharides were separated from the peptide structure and sorted using a coupled Gas Chromatography-Mass Spectrometry Automass apparatus (Finnigan). Molar ratio was determined in reference to a known internal standard and to a 3 Mannose content of a classical mammalian N-Glycan.

Such an analysis gave the following molar ratio for CHO-derived hIL-7

TABLE 5

| Monosaccharide | Fuc | Gal | Man | GalNAc | GlcNAc | NeuAc |
|---|---|---|---|---|---|---|
| Molecular Mass | 164 | 180 | 180 | 221 | 221 | 309 |
| Peack Surface | 43382 | 179120 | 310124 | 33650 | 344476 | 423587 |
| N° of nanomoles | 5.41 | 24.76 | 22.15 | 5.26 | 27.29 | 20.94 |
| Molar ratio | 0.73 | 3.35 | 3 | 0.71 | 3.69 | 2.83 |

Sites-specific N-glycan pattern heterogeneity of the CHO-derived hIL-7 was assayed by endoprotease digestion, followed by fractionation and Mass Spectrometry analyses of the generated peptides.

Purified samples were digested with Tripsin or other endoproteases so as to generate glycopeptides corresponding to each N-glycosylation site of the expressed IL-7. Each glycopeptide was identified by N-terminal microsequencing and by its specific retention time when analyzed by reverse phase HPLC. Each glycopeptide was therefore purified from the other ones. The heterogeneity of the N-glycans born by the glycopeptide was analysed by MALDI-TOF MS (Q Star, Applied Biosystems). The m/z values corresponding to each peak of the MS spectrum allowed identification of the N-Glycan pattern at a designated site of the hIL-7.

O-glycosylation was assayed via the use of O-glycan specific lectins (Lectin Blot, see FIG. 11).

Purified CHO-derived hIL-7 samples were separated by SDS-PAGE analysis and blotted to PVDF membranes. Immobilized proteins were probed with (but not limited to) peroxidase-labelled PNA (peanut agglutinin) and/or MM (*Maackia amurensis* agglutinin) and stained for visualization.

Glycan heterogeneity and composition were also determined via the use of Lectin affinity to the purified CHO-derived hIL-7.

An array of lectins having affinity for N- and O-glycan structures was selected and used to coat 96 well microplates. Identical amounts of recombinant purified IL-7 preparations were incubated into lectin coated microplate wells. During this step, according to the affinity of a given lectin to the glycan decoration of IL-7, different amount of IL-7 were kept bound to the lectin. Revelation was conducted by incubating an IL-7 specific antibody coupled to Biotin. The Lectin—IL-7—Ab sandwich was revealed with a streptavidin-peroxidase conjugate.

Eight different lectins were used to characterize the IL-7 purified samples. Each lectin specifically recognizes sugar moieties. Glycan motifs and structure specificity are presented in Table 6.

Table 6: summary of the pattern of sugar moieties recognized by lectins and inventory of their glycan motifs and structure specificity.

LEA is the lectin from *Lycopersicon esculentum*,
WGA from *Triticum vulgare*,
UEA.I from *Ulex europeus*,
MM from *Maackia amurensis*,
ACA from *Amaranthus caudatus*,
AIA from *Artocarpus intergrifolia*,
ABA from *Agaricus bisporus*,
PHA.L from *Phaseolus vulgaris*.

TABLE 6

| Name | Glc | GlcNAc | Man | Fuc | NeuAc | GalNAc | Gal | Glycans structure specificity |
|---|---|---|---|---|---|---|---|---|
| LEA | | + | | | | | | GlcNAcβ4GlcNAc and N-acetyllactosamine oligomers |
| WGA | | + | | | + | | | GlcNAc, core of N- linked Glycans, Neu5ac |
| UEAI | | | | + | | | | Fucose |
| MAA | | | | | + | | | Neu5Acα-3Galb4GlcNAc- |
| ACA | | | | | | + | | Galb3GalNAcα-O-R (T-antigen) |
| AIA | | | | | | | + | Galα6 or Galβ3GalNAc (T-antigen), lactose |
| ABA | | | | | | | + | Gal-GalNAcα-O-R, O-linked glycans |
| PHAL | | | | | | | | Galb4GlcNAcβ6Man, branched complex N-glycans |

Results are presented in FIG. 12.

Lectins clearly demonstrate differential affinity, providing information on the general structure of the accessible glycan decoration of the purified IL-7 protein in solution. Thus, ACA, ABA and AIA have affinity for Gal and GalNAc. All three lectins respond positively suggesting the presence of N- and O-Glycan structures bearing these monosaccharides. The specific signal obtained with ABA reveals the presence of O-glycans structures. ACA has a weak signal compared to AIA and to a lesser extent ABA. This reveals that the 0 glycans are extended with little GaINAc as terminal residue.

LEA has affinity for GaINAc indicating the presence of N-Glycan structures. Among the GlcNAc-specific lectins tested (data not shown), only those with affinity for N-acetyl-lactosamine reveal a positive signal.

WGA presented a weak signal due to a low binding affinity to core structures of N-linked glycans. Highly complex N-Glycans mask the core structure and render lectin affinity difficult to operate.

UEA.I has specific activity to the presence of branched fucose. Binding is rather weak indicating an uncomplete but effective fucosylation of the N-Glycans.

MAA has affinity to terminal sialic acids. MAA signal is strong indicating an effective sialylation on both N and O-glycans.

PHA.L has affinity to complex branched structures of N-Glycan and showed a strong signal, corroborating the results of MAA. PHA-L signal suggests the presence of large tri or tetra-antennary N-glycans.

Most typical mammalian O-glycans characterized on CHO-derived hIL-7 (when applicable):

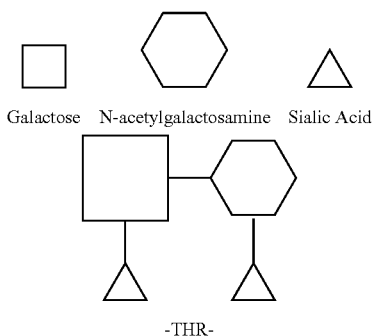

Altogether, these analyses indicate that the CHO cell-based expression system used generates human IL-7 complex (triantennary) N-linked oligosaccharide, as depicted in the following figure, branched to their ASN residue at position 70, 91 and 116 with high partial to complete sialilation, up to 10 sialic acid residues. Also, the CHO-derived IL-7 contains an O-glycan at position T110.

Therefore, although bearing complex sialilated N-glycans and O-glycans, the IL-7 purified batch still contains a mixture of fully and partially glycosylated proteins.

Example F

Drug Substance to Drug Product

Formulation, Storage and Long Term Stability of the Recombinant CHO Cell Expressed hIL-7

Search for optimal formulation of the drug substance was conducted throughout a combinatory matrix study to evaluate the impact of various stress conditions (temperature, buffer, pH, tonicity modifier concentration, agitation, intense illumination) on the long term stability of the purified protein.

Highly complex purified recombinant human IL-7 was shown to be stable in Acetate as well as succinate buffers, at a concentration ranging between 5 to 50 mM. Adequate pHs were chosen from pH=5.0 to 7.0 and ideal storage temperatures were between −20° C. to +4° C.

Sugars and low concentration of surfactants (Polysorbate polymers) may be added to the preparation to prevent non covalent soluble aggregation.

In such conditions, IL-7 could be stored at +4° C. (in liquid form) at a concentration ranging from 0.5 to 8.0 mg/ml, preferably from 2.0 to 4.0 mg/ml, for more than 12 months. The pharmaceutical composition in liquid form has an improved stability profile.

Example G

Proliferative Activity Analysis of Mammalian Cells-Derived Recombinant Human IL-7 in a Specific Bioassay The biological activity of mammalian cell-derived recombinant human IL-7 was evaluated in a specific bioassay onto a murine pre-B cell line derived from bone marrow cells from CBA/C57BL mice, PB-1 (German Cell Bank DSMZ, Deutsche Sammiung von Mikrooganismen und Zellkulturen), strictly dependent on IL-7 for growth (Mire-Sluis et al.; 2000; J. Immunol. Methods; 236:71-76). These cells were maintained in culture in commercial IL-7 containing medium and starved for IL-7 prior to conducting the bioassay.

Bioassays were run with IL-7 samples to be tested, in parallel to a known E. coli-derived IL-7 positive control and a negative control lacking IL-7.

IL-7, from control or samples, added to the starved cell culture, induced the dose dependent re-initiation of cell proliferation during which radiolabelled thymidine (3H-Tdr, Amersham) was incorporated by dividing cells. The amount of labelling was pulsed and measured in counts per minute (cpm) in a liquid scintillation Beta counter (Wallack).

Alternatively, this bioassay may be conducted while using a dye marker reflecting the general metabolism of the cell, such as MTT dye (3-(4,5-dimethylthiazole-2-yl)-2,5-diphenyl tetrazolium, reduced by mitochondrial RedOx activity) or MTS dye (3-(4,5-dimethylthiazol-2-yl)-5-(3-carboxymethoxyphenyl)-2-(4-sulfophenyl)-2H-tetrazolium).

Serial dilutions of both the positive control and the samples to be tested allowed plotting the number of cpm in relation to the amount of sample/control assayed.

FIG. 13 presents dose-response kinetic data and curves obtained routinely in a typical bioassay: the PB-1 cell growth was induced by unglycosylated r-hIL-7 (expressed in E. coli) or highly glycosylated r-hIL-7 (produced in mammalian cells). (Data points represent the mean ±SD of triplicate determination).

FIG. 14 presents dose-response kinetic data and curves obtained routinely in a typical bioassay: the PB-1 cell growth was induced by unglycosylated r-hIL-7 (expressed in E. coli), highly glycosylated or hyperglycosylated r-hIL-7 (produced in mammalian cells). (Data points represent the mean ±SD of triplicate determination).

The important parameter to be considered for each sample was the ED50=concentration (ng/ml) giving half-maximal activity. A higher ED50 meaning a lower activity.

Activity comparability between IL-7 batches is addressed via the analysis of the dose response curve parameter, such as slope coefficient, maximal activity. From all curve parameters an ED50 concentration (in ng/ml) pools parameters variation together. ED50 corresponds to the IL-7 dose necessary to induce one half of the possible maximal induction activity in vitro. In this regard, highly bioactive molecules correspond to low ED50 values whereas higher ED50 concentrations will be typical from less bioactive IL-7 preparations in vitro.

Nevertheless, in vitro bioactivity differences are not necessarily representative of similar in vivo bioactivity differences in the present invention.

Example H

In Vivo Evaluation the Immunogenicity of Hyperglycosylated IL-7 Polypeptide in Primates Simian hyperglycosylated IL-7 (sIL-7) expressed in CHO cell line (Examples A2, A6 and B) and purified according to Example D, was evaluated in vivo for occurrence of potential immunogenicity, following sIL-7 repeated administrations in normal primates.

Naïve young adult Cynomolgus monkeys (*Macaca fascicularis*)(n=4) were entered into the study and received hyperglycosylated sIL-7 at the dose level of 100 µg/kg/injection. Treated animals received a total of 6 subcutaneous administrations of IL-7 over a period of five consecutive weeks. The animals were clinically observed over a two month period. Blood specimens were collected, at different time points, throughout the study: on day 1 before sIL-7 administration, on day 37 and at the end of the study.

All animals survived the study and had no adverse reaction to sIL-7 therapy. Administration of sII-7 was locally well tolerated. When tested by interference in a specific ELISA assay aimed at detecting binding antibodies, no anti-IL-7 antibodies were detected in the serum of all treated animals. In comparison, *E. coli*-derived recombinant IL-7, although produced as a highly purified drug product, induced, in similar protocol, the production of high titers of IL-7-binding antibodies in sera ranging from 1:400 up to 1:5000.

Example I

In Vivo Biological Activity of Hyperglycosylated IL-7 Polypeptide in Primates Human hyperglycosylated IL-7 (hIL-7) expressed in CHO cell line (Examples A1, A6 and B) and purified as in Example D, was evaluated in vivo for determination of pharmacokinetic and pharmacodynamic profiles of hIL-7 in normal primates.

Naïve young adult Cynomolgus monkeys (*Macaca fascicularis*) were entered into the study and divided into two groups: untreated n=2 and hIL-7 100 µg/kg/injection n=2. The treated animals received single subcutaneous administration of hIL-7. The animals were clinically observed during 45 days. Blood specimens were collected, at different time points, throughout the study: on days 1 (0, 3, 6, 9 and 12 hours post injection), 2, 3, 4, 7, 21 and 45.

Administration of hIL-7 was well tolerated with no local reaction at injection site. Following single subcutaneous administration of hIL-7 in macaques, the pharmacokinetic pattern and parameters of hIL-7 were established from the first 72 hours:

- The plasma profile showed a bi-exponential decline after peak absorption.
- The observed product half-life in plasma was in the range of 30/40 hours. This half-life is significantly increased when compared to the half-life observed with the *E. coli*-derived recombinant IL-7 (5 to 8 hours) administered in the same conditions. This reflects an improved in vivo stability of the hyperglycosylated IL-7 polypeptide in blood.
- The mean residence time (MRT) was 40 hours versus around 10 hrs with the *E. coli* product.
- The time to reach a maximum concentration was 180 minutes.

In conclusion, the pharmacokinetic study shows that the hyperglycosylated IL-7 polypeptide of this invention displays an improved and prolonged pharmacokinetic profile, which translates into improved pharmacodynamic effects. The single injection of hIL-7 at 100 µg/kg induced a significant increase in peripheral $CD3^+$ $CD4^+$ and $CD3^+$ $CD8^+$ T cell numbers, respectively 200% and 170% of changes from the baseline pre-treatment values. The number of lymphocyte T cells (CD4 and CD8) expressing the specific IL-7 receptor alpha chain (CD127) transiently decreases in peripheral blood as early as 6 hours post injection. Lymphocyte T cells expressing CD127 reappeared, in peripheral blood, 48 hours post injection and returned to baseline values only 7 days post injection. Following single subcutaneous administration of *E. coli*-derived recombinant IL-7, the full return to baseline values of lymphocyte T cells expressing CD127 occurred 4 days post injection. The kinetic of receptor occupancy of hyperglycosylated IL-7 polypeptide in more longer compared to *E. coli*-derived recombinant IL-7, reflecting the longer half-life of hyperglycosylated IL-7 polypeptide in primates as shown below. These results are in line with previous results showing that although IV administration of IL-7 results in a better bioavailability, this does not translate into improved pharmacokinetic effects, in fact the extended delivery profile obtained by sub cutaneous injection is more efficient than the acute delivery profile obtained after IV injection. Here the hyperglycosylation of the protein induces a prolonged kinetic profile, which in turn translates into an improved pharmacodynamic activity. In view of this extended profile also it is also expected an improved clinical tolerance, because drug sides effects are usually linked to peak concentrations.

The invention claimed is:

1. A hyperglycosylated, IL-7 composition, wherein said composition comprises a mammalian IL-7 polypeptide having at least three glycosylated amino acid residues, an average isoelectric point less than 6.5 and an average molecular weight greater than 27 KDa as determined by SDS gel electrophoresis.

2. The composition of claim 1, wherein the mammalian IL7 polypeptide is a human IL-7 polypeptide comprising SEQ ID NO: 1.

3. The composition of claim 1, wherein the mammalian IL-7 polypeptide is a canine IL-7 polypeptide comprising SEO ID NO: 7.

4. The composition of claim 1, wherein the glycosylated amino acid residues are located at glycosylation sites which are naturally present and/or artificially created in the IL-7 polypeptide sequence.

5. The composition of claim 4, wherein the mammalian IL-7 polypeptide is SEQ ID NO: 1 and wherein the glycosylation sites are selected from Asn residues at positions 70, 91 and 116; Thr at position 110, any artificially created glycosylation sites as listed in Table 1, or any combination thereof.

6. The composition of claim 5, wherein said IL-7 polypeptides comprise N-linked carbohydrate selected from:
   a) a mammalian type sugar chain;
   b) a sugar chain comprising a complex N-carbohydrate chain;
   c) a sugar chain sialylated by alpha2,6-sialyltransferase or alpha2,3-sialyltransferase; and/or
   d) a sialylated sugar chain displaying between 3 to 30 sialyl-N-acetylgalactosamine.

7. The composition of claim 5, wherein said IL-7 polypeptides comprise O-linked carbohydrate chain(s) with a terminal sialic acid residue.

8. The composition of claim 5, wherein said glycosylation sites are glycosylated with carbohydrate chains that comprise tetra-antenary to biantenary structures with partial or complete terminal sialylation.

9. The composition of claim 8, wherein said glycosylafion sites are glycosylated with carbohydrate chains that have a triantenary structure and tri- or bi-sialylation and/or a diantenary structure with disialylation.

10. The composition of claim 1, wherein said IL-7 hyperglycosylated polypeptides show an in vivo extended half-life and mean residence time as compared to non-glycosyated IL-7 polypeptides.

11. The composition of claim 4, comprising an IL-7 polypeptide with at least one artificially created glycosylation site, wherein said polypeptide comprises SEQ ID NO: 1 with one or more of the following amino acid substitutions: Lys28Asn-Ile30Ser-Ile30Thr-Ile30Asn-Ser32Thr-Leu35Ser-Leu35Thr-Glu38Ser-Glu38Thr-Phe39Ser-Phe39Thr-Phe42Ser-Phe42Thr-Glu52Ser-Glu52Thr-Val82Asn-Glu84Thr-Glu84Ser-Lys97Asn-Arg99Thr-Arg99Ser-Ala102Asn-Leu104Thr-Leu104Ser-Leu104Asn-Glu106Thr-Glu106Ser-Leu128Ser-Leu128Thr-Ile145Asn-Met147Thr-Met147Ser-Met147Asn or Thr149Ser.

12. The composition of claim 1, produced by:
   a) culturing, in a fed-batch or perfusion mode, a recombinant host cell comprising a recombinant nucleic acid molecule encoding an IL-7 polypeptide;
   b) collecting the IL-7 polypeptide produced from said cell; and
   c) purifying said IL-7 polypeptide by a method comprising at least a step of hydrophobic interaction chromatography, ion exchange chromatography, affinity chromatography or gel filtration chromatography, either alone or in various combinations, so as to obtain a composition which comprises at least 80% mammalian IL-7 polypeptides having at least three glycosylated amino acid residues, an average isoelectric point less than 6.5 and an average molecular weight greater than 27 KDa as determined by SDS gel electrophoresis.

13. A hyperglycosylated, IL-7 composition, wherein said composition contains mammalian IL-7 polypeptides having an average isoelectric point less than 6.5 and an average molecular weight greater than 27 KDa as determined by SDS gel electrophoresis, wherein said mammalian IL-7 polypeptides comprise SEQ ID NO: 1 with the following amino acid chances: Lys28Asn and Ile30Ser; Lys28Asn and Ile30Thr; Ile30Asn and Ser32Thr; Leu35Ser; Leu35Thr; Glu38Ser; Glu38Thr; Phe39Ser; Phe39Thr; Phe42Ser; Phe42Thr; Glu52Ser; Glu52Thr; Val82Asn and Glu84Ser; Val82Asn and Glu84Thr; Lys97Asn and Arg99Ser; Lys97Asn and Arg99Thr; Ala102Asn and Leu104Ser; Ala102Asn; Leu104Thr; Leu104Asn and Glu106Ser; Leu104Asn and Glu106Thr; Leu128Ser; Leu128Thr; Ile145Asn and Met147Ser; Ile145Asn and Met147Thr; or Met147Asn and Thr149Ser.

* * * * *

UNITED STATES PATENT AND TRADEMARK OFFICE
CERTIFICATE OF CORRECTION

PATENT NO. : 7,708,985 B2  Page 1 of 2
APPLICATION NO. : 11/996176
DATED : May 4, 2010
INVENTOR(S) : Michel Christian Morre et al.

It is certified that error appears in the above-identified patent and that said Letters Patent is hereby corrected as shown below:

Column 7,
Line 20, "MM from" should read --MAA from--.

Column 8,
Line 38, "natural "variants," or homologs" should read --natural variants, homologs--.

Column 10,
Line 45, "Gln 22" should read --Gln 22--.

Column 14,
Line 27, "In an other" should read --In another--.
Line 33, "In an other" should read --In another--.

Column 22,
Line 25, "chicken Pactine" should read --chicken βactine--.

Column 29,
Line 37, "NotI and PmII" should read --NotI and PmII--.
Line 38, "NotI/Pmi" should read --NotI/PmII--.

Column 32,
Line 40, "each peack" should read --each peak--.

Column 35,
Table 5, Line 3, "Peack Surface" should read --Peak Surface--.
Line 55, "MM" should read --MAA--.

Column 36,
Line 26, "MM" should read --MAA--.

Signed and Sealed this

Thirteenth Day of July, 2010

David J. Kappos
*Director of the United States Patent and Trademark Office*

Column 38,
Line 15, "Sammiung" should read --Sammlung--.

Column 39,
Line 21, "sII-7" should read --sIL-7--.

Column 40,
Line 34, "polypeptide in more longer" should read --polypeptide is longer--.

Column 53,
Line 20 claim 1, "IL7" should read --IL-7--.
Line 50 claim 9, "glycosylafion" should read --glycosylation--.
Line 52 claim 9, "triantenary" should read --tri-antenary--.

SEQUENCE LISTING

```
<160> NUMBER OF SEQ ID NOS: 19

<210> SEQ ID NO 1
<211> LENGTH: 152
<212> TYPE: PRT
<213> ORGANISM: Homo sapiens

<400> SEQUENCE: 1

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30
```

```
Asn Cys Leu Asn Asn Glu Phe Asn Phe Phe Lys Arg His Ile Cys Asp
         35                  40                  45
Ala Asn Lys Glu Gly Met Phe Leu Phe Arg Ala Ala Arg Lys Leu Arg
 50                  55                  60
Gln Phe Leu Lys Met Asn Ser Thr Gly Asp Phe Asp Leu His Leu Leu
 65                  70                  75                  80
Lys Val Ser Glu Gly Thr Thr Ile Leu Leu Asn Cys Thr Gly Gln Val
                 85                  90                  95
Lys Gly Arg Lys Pro Ala Ala Leu Gly Glu Ala Gln Pro Thr Lys Ser
                100                 105                 110
Leu Glu Glu Asn Lys Ser Leu Lys Glu Gln Lys Lys Leu Asn Asp Leu
             115                 120                 125
Cys Phe Leu Lys Arg Leu Leu Gln Glu Ile Lys Thr Cys Trp Asn Lys
130                 135                 140
Ile Leu Met Gly Thr Lys Glu His
145                 150
```

<210> SEQ ID NO 2
<211> LENGTH: 540
<212> TYPE: DNA
<213> ORGANISM: Homo sapiens
<220> FEATURE:
<221> NAME/KEY: CDS
<222> LOCATION: (1)..(537)
<223> OTHER INFORMATION: EPy7-hIL7-optimized

<400> SEQUENCE: 2

```
atg ggt gtt cat gaa tgt cct gct tgg ttg tgg ttg ttg tct ttg         48
Met Gly Val His Glu Cys Pro Ala Trp Leu Trp Leu Leu Ser Leu
 1               5                  10                  15 ttg tct ttg gtt ctg ttg cct gta gcc tct gat tgc gat att gaa ggg    96
Leu Ser Leu Val Leu Leu Pro Val Ala Ser Asp Cys Asp Ile Glu Gly
                 20                  25                  30 aaa gat ggg aag cag tat gag tcc gtg ctg atg gtg agc atc gat caa  144
Lys Asp Gly Lys Gln Tyr Glu Ser Val Leu Met Val Ser Ile Asp Gln
             35                  40                  45 ttg ttg gac tcc atg aaa gaa att ggg agt aac tgc ctg aat aac gaa  192
Leu Leu Asp Ser Met Lys Glu Ile Gly Ser Asn Cys Leu Asn Asn Glu
 50                  55                  60 ttt aac ttc ttt aag cgc cat atc tgt gat gct aat aag gaa ggt atg  240
Phe Asn Phe Phe Lys Arg His Ile Cys Asp Ala Asn Lys Glu Gly Met
 65                  70                  75                  80 ttt ttg ttc cgc gct gct cgg aag ttg cgc cag ttc ctt aag atg aac  288
Phe Leu Phe Arg Ala Ala Arg Lys Leu Arg Gln Phe Leu Lys Met Asn
                 85                  90                  95 tct act ggt gat ttc gat ctc cac ctc ctg aaa gtt tcc gaa ggg act  336
Ser Thr Gly Asp Phe Asp Leu His Leu Leu Lys Val Ser Glu Gly Thr
                100                 105                 110 act atc ctg ttg aac tgc act ggc cag gtt aaa gga aga aaa ccc gct  384
Thr Ile Leu Leu Asn Cys Thr Gly Gln Val Lys Gly Arg Lys Pro Ala
             115                 120                 125 gcc ctg ggt gaa gcc caa ccg aca aag agt ttg gaa gaa aat aaa tct  432
Ala Leu Gly Glu Ala Gln Pro Thr Lys Ser Leu Glu Glu Asn Lys Ser
130                 135                 140 ttg aag gaa cag aag aag ctg aac gac ttg tgt ttc ctg aag cgc ctg  480
Leu Lys Glu Gln Lys Lys Leu Asn Asp Leu Cys Phe Leu Lys Arg Leu
145                 150                 155                 160 ttg cag gag att aag act tgt tgg aat aag atc ttg atg ggg act aag  528
Leu Gln Glu Ile Lys Thr Cys Trp Asn Lys Ile Leu Met Gly Thr Lys
```

```
                    165                 170                 175
gag cat tga taa                                                      540
Glu His <210> SEQ ID NO 3
<211> LENGTH: 178
<212> TYPE: PRT
<213> ORGANISM: Homo sapiens

<400> SEQUENCE: 3

Met Gly Val His Glu Cys Pro Ala Trp Leu Trp Leu Leu Leu Ser Leu
1               5                   10                  15

Leu Ser Leu Val Leu Leu Pro Val Ala Ser Asp Cys Asp Ile Glu Gly
            20                  25                  30

Lys Asp Gly Lys Gln Tyr Glu Ser Val Leu Met Val Ser Ile Asp Gln
        35                  40                  45

Leu Leu Asp Ser Met Lys Glu Ile Gly Ser Asn Cys Leu Asn Asn Glu
    50                  55                  60

Phe Asn Phe Phe Lys Arg His Ile Cys Asp Ala Asn Lys Glu Gly Met
65                  70                  75                  80

Phe Leu Phe Arg Ala Ala Arg Lys Leu Arg Gln Phe Leu Lys Met Asn
                85                  90                  95

Ser Thr Gly Asp Phe Asp Leu His Leu Leu Lys Val Ser Glu Gly Thr
            100                 105                 110

Thr Ile Leu Leu Asn Cys Thr Gly Gln Val Lys Gly Arg Lys Pro Ala
        115                 120                 125

Ala Leu Gly Glu Ala Gln Pro Thr Lys Ser Leu Glu Glu Asn Lys Ser
    130                 135                 140

Leu Lys Glu Gln Lys Lys Leu Asn Asp Leu Cys Phe Leu Lys Arg Leu
145                 150                 155                 160

Leu Gln Glu Ile Lys Thr Cys Trp Asn Lys Ile Leu Met Gly Thr Lys
                165                 170                 175

Glu His

<210> SEQ ID NO 4
<211> LENGTH: 537
<212> TYPE: DNA
<213> ORGANISM: Simian
<220> FEATURE:
<221> NAME/KEY: CDS
<222> LOCATION: (1)..(537)
<223> OTHER INFORMATION: EPy7-sIL-7 Optimized

<400> SEQUENCE: 4 atg ggt gtt cat gaa tgt cct gct tgg ttg tgg ttg ttg ttg tct ttg    48
Met Gly Val His Glu Cys Pro Ala Trp Leu Trp Leu Leu Leu Ser Leu
1               5                   10                  15 ttg tct ttg gtt ctg ttg cct gta gcc tct gat tgc gat att gaa ggg    96
Leu Ser Leu Val Leu Leu Pro Val Ala Ser Asp Cys Asp Ile Glu Gly
            20                  25                  30 aaa gat ggg aag cag tat gag tcc gtg ctg atg gtg agc atc gat caa   144
Lys Asp Gly Lys Gln Tyr Glu Ser Val Leu Met Val Ser Ile Asp Gln
        35                  40                  45 ttg ttg gac tcc atg aaa gaa att ggg agt aac tgc ctg aat aac gaa   192
Leu Leu Asp Ser Met Lys Glu Ile Gly Ser Asn Cys Leu Asn Asn Glu
    50                  55                  60 ttt aac ttc ttt aag cgc cat ctg tgt gat gat aat aag gaa ggt atg   240
Phe Asn Phe Phe Lys Arg His Leu Cys Asp Asp Asn Lys Glu Gly Met
65                  70                  75                  80
```

```
ttt ttg ttc cgc gct gct cgg aag ttg cgc cag ttc ctt aag atg aac      288
Phe Leu Phe Arg Ala Ala Arg Lys Leu Arg Gln Phe Leu Lys Met Asn
                85                  90                  95 tct act ggt gat ttc gat ctc cac ctc ctg aaa gtt tcc gaa ggg act      336
Ser Thr Gly Asp Phe Asp Leu His Leu Leu Lys Val Ser Glu Gly Thr
            100                 105                 110 act atc ctg ttg aac tgc act ggc aag gtt aaa gga aga aaa ccc gct      384
Thr Ile Leu Leu Asn Cys Thr Gly Lys Val Lys Gly Arg Lys Pro Ala
        115                 120                 125 gcc ctg ggt gaa ccc caa ccg aca aag agt ttg gaa gaa aat aaa tct      432
Ala Leu Gly Glu Pro Gln Pro Thr Lys Ser Leu Glu Glu Asn Lys Ser
    130                 135                 140 ttg aag gaa cag aag aag ctg aac gac tcc tgt ttc ctg aag cgc ctg      480
Leu Lys Glu Gln Lys Lys Leu Asn Asp Ser Cys Phe Leu Lys Arg Leu
145                 150                 155                 160 ttg cag aag att aag act tgt tgg aat aag atc ttg atg ggg act aag      528
Leu Gln Lys Ile Lys Thr Cys Trp Asn Lys Ile Leu Met Gly Thr Lys
                165                 170                 175 gag cat tga                                                          537
Glu His <210> SEQ ID NO 5
<211> LENGTH: 178
<212> TYPE: PRT
<213> ORGANISM: Simian

<400> SEQUENCE: 5

Met Gly Val His Glu Cys Pro Ala Trp Leu Trp Leu Leu Leu Ser Leu
1               5                   10                  15

Leu Ser Leu Val Leu Pro Val Ala Ser Asp Cys Asp Ile Glu Gly
            20                  25                  30

Lys Asp Gly Lys Gln Tyr Glu Ser Val Leu Met Val Ser Ile Asp Gln
        35                  40                  45

Leu Leu Asp Ser Met Lys Glu Ile Gly Ser Asn Cys Leu Asn Asn Glu
    50                  55                  60

Phe Asn Phe Phe Lys Arg His Leu Cys Asp Asp Asn Lys Glu Gly Met
65                  70                  75                  80

Phe Leu Phe Arg Ala Ala Arg Lys Leu Arg Gln Phe Leu Lys Met Asn
                85                  90                  95

Ser Thr Gly Asp Phe Asp Leu His Leu Leu Lys Val Ser Glu Gly Thr
            100                 105                 110

Thr Ile Leu Leu Asn Cys Thr Gly Lys Val Lys Gly Arg Lys Pro Ala
        115                 120                 125

Ala Leu Gly Glu Pro Gln Pro Thr Lys Ser Leu Glu Glu Asn Lys Ser
    130                 135                 140

Leu Lys Glu Gln Lys Lys Leu Asn Asp Ser Cys Phe Leu Lys Arg Leu
145                 150                 155                 160

Leu Gln Lys Ile Lys Thr Cys Trp Asn Lys Ile Leu Met Gly Thr Lys
                165                 170                 175

Glu His

<210> SEQ ID NO 6
<211> LENGTH: 480
<212> TYPE: DNA
<213> ORGANISM: canine
<220> FEATURE:
<221> NAME/KEY: CDS
<222> LOCATION: (1)..(480)
```

<223> OTHER INFORMATION: EPy7-cIL-7

<400> SEQUENCE: 6

```
atg ggt gtt cat gaa tgt cct gct tgg ttg tgg ttg ttg tct ttg         48
Met Gly Val His Glu Cys Pro Ala Trp Leu Trp Leu Leu Ser Leu
1               5                   10                  15 ttg tct ttg gtt ctg ttg cct gta gcc tct gat tgt gat att gaa ggc     96
Leu Ser Leu Val Leu Leu Pro Val Ala Ser Asp Cys Asp Ile Glu Gly
            20                  25                  30 aaa gac ggc aga gag tat cag cac gtt cta atg atc agc atc aat gac    144
Lys Asp Gly Arg Glu Tyr Gln His Val Leu Met Ile Ser Ile Asn Asp
        35                  40                  45 ttg gac atc atg ata aaa aat cgt acc aat tgc tcg aat aat gaa cct    192
Leu Asp Ile Met Ile Lys Asn Arg Thr Asn Cys Ser Asn Asn Glu Pro
50                  55                  60 aac att tta aaa aaa cat gca tgt gat gat aat aag gaa ggt atg ttt    240
Asn Ile Leu Lys Lys His Ala Cys Asp Asp Asn Lys Glu Gly Met Phe
65                  70                  75                  80 tta tat cgt gct gct cac aag ttg aag caa ttt gtt aaa gtg aat aac    288
Leu Tyr Arg Ala Ala His Lys Leu Lys Gln Phe Val Lys Val Asn Asn
                85                  90                  95 agt gag gat ttc aat ctc cac tta tca aga gtt tca cag ggc aca tta    336
Ser Glu Asp Phe Asn Leu His Leu Ser Arg Val Ser Gln Gly Thr Leu
            100                 105                 110 caa ttg ttg aac tgt act ccc aag gaa gac aat aaa tct tta aag gaa    384
Gln Leu Leu Asn Cys Thr Pro Lys Glu Asp Asn Lys Ser Leu Lys Glu
        115                 120                 125 cag aga aaa cag aag agc ttg tgt tcc cta ggg ata cta cta caa aag    432
Gln Arg Lys Gln Lys Ser Leu Cys Ser Leu Gly Ile Leu Leu Gln Lys
    130                 135                 140 ata aaa act tgt tgg aac aaa att ttg agg ggc tct aaa gaa cat tga    480
Ile Lys Thr Cys Trp Asn Lys Ile Leu Arg Gly Ser Lys Glu His
145                 150                 155
```

<210> SEQ ID NO 7
<211> LENGTH: 159
<212> TYPE: PRT
<213> ORGANISM: canine

<400> SEQUENCE: 7

```
Met Gly Val His Glu Cys Pro Ala Trp Leu Trp Leu Leu Ser Leu
1               5                   10                  15

Leu Ser Leu Val Leu Leu Pro Val Ala Ser Asp Cys Asp Ile Glu Gly
            20                  25                  30

Lys Asp Gly Arg Glu Tyr Gln His Val Leu Met Ile Ser Ile Asn Asp
        35                  40                  45

Leu Asp Ile Met Ile Lys Asn Arg Thr Asn Cys Ser Asn Asn Glu Pro
50                  55                  60

Asn Ile Leu Lys Lys His Ala Cys Asp Asp Asn Lys Glu Gly Met Phe
65                  70                  75                  80

Leu Tyr Arg Ala Ala His Lys Leu Lys Gln Phe Val Lys Val Asn Asn
                85                  90                  95

Ser Glu Asp Phe Asn Leu His Leu Ser Arg Val Ser Gln Gly Thr Leu
            100                 105                 110

Gln Leu Leu Asn Cys Thr Pro Lys Glu Asp Asn Lys Ser Leu Lys Glu
        115                 120                 125

Gln Arg Lys Gln Lys Ser Leu Cys Ser Leu Gly Ile Leu Leu Gln Lys
    130                 135                 140
```

Ile Lys Thr Cys Trp Asn Lys Ile Leu Arg Gly Ser Lys Glu His
145                 150                 155

<210> SEQ ID NO 8
<211> LENGTH: 18
<212> TYPE: DNA
<213> ORGANISM: Artificial sequence
<220> FEATURE:
<223> OTHER INFORMATION: description of artificial sequence: mutated
      domain

<400> SEQUENCE: 8
ctgaataacg aaactaac                                                    18

<210> SEQ ID NO 9
<211> LENGTH: 12
<212> TYPE: DNA
<213> ORGANISM: Artificial sequence
<220> FEATURE:
<223> OTHER INFORMATION: description of artificial sequence: mutated
      domain

<400> SEQUENCE: 9
aacttcacta ag                                                          12

<210> SEQ ID NO 10
<211> LENGTH: 12
<212> TYPE: DNA
<213> ORGANISM: Artificial sequence
<220> FEATURE:
<223> OTHER INFORMATION: description of artificial sequence: mutated
      domain

<400> SEQUENCE: 10
gccaacggta cc                                                          12

<210> SEQ ID NO 11
<211> LENGTH: 15
<212> TYPE: DNA
<213> ORGANISM: Artificial sequence
<220> FEATURE:
<223> OTHER INFORMATION: description of artificial sequence: mutated
      domain

<400> SEQUENCE: 11
ctgaacgaca gctgt                                                       15

<210> SEQ ID NO 12
<211> LENGTH: 12
<212> TYPE: DNA
<213> ORGANISM: Artificial sequence
<220> FEATURE:
<223> OTHER INFORMATION: description of artificial sequence: mutated
      domain

<400> SEQUENCE: 12
atcttgaacg gg                                                          12

<210> SEQ ID NO 13
<211> LENGTH: 25
<212> TYPE: PRT
<213> ORGANISM: homo sapiens

<400> SEQUENCE: 13

Met Phe His Val Ser Phe Arg Tyr Ile Phe Gly Leu Pro Pro Leu Ile
1               5                   10                  15

-continued

Leu Val Leu Leu Pro Val Ala Ser Ser
            20                  25

<210> SEQ ID NO 14
<211> LENGTH: 27
<212> TYPE: PRT
<213> ORGANISM: homo sapiens

<400> SEQUENCE: 14

Met Gly Val His Glu Cys Pro Ala Trp Leu Trp Leu Leu Leu Ser Leu
1               5                   10                  15

Leu Ser Leu Pro Leu Gly Leu Pro Val Leu Gly
            20                  25

<210> SEQ ID NO 15
<211> LENGTH: 17
<212> TYPE: PRT
<213> ORGANISM: homo sapiens

<400> SEQUENCE: 15

Met Leu Leu Leu Leu Leu Leu Gly Leu Arg Leu Gln Leu Ser Leu
1               5                   10                  15

Gly

<210> SEQ ID NO 16
<211> LENGTH: 20
<212> TYPE: PRT
<213> ORGANISM: homo sapiens

<400> SEQUENCE: 16

Met Glu Thr Asp Thr Leu Leu Leu Trp Val Leu Leu Leu Trp Val Pro
1               5                   10                  15

Gly Ser Thr Gly
            20

<210> SEQ ID NO 17
<211> LENGTH: 19
<212> TYPE: PRT
<213> ORGANISM: homo sapiens

<400> SEQUENCE: 17

Met Lys Leu Val Phe Leu Val Leu Leu Phe Leu Gly Ala Leu Gly Val
1               5                   10                  15

Ala Leu Ala

<210> SEQ ID NO 18
<211> LENGTH: 20
<212> TYPE: PRT
<213> ORGANISM: homo sapiens

<400> SEQUENCE: 18

Met Ala Arg Pro Leu Cys Thr Leu Leu Leu Leu Met Ala Thr Leu Ala
1               5                   10                  15

Val Ala Leu Ala
            20

<210> SEQ ID NO 19
<211> LENGTH: 26
<212> TYPE: PRT
<213> ORGANISM: Artificial sequence
<220> FEATURE:
<223> OTHER INFORMATION: description of artificial sequence: chimeric
      signal peptide

```
<400> SEQUENCE: 19

Met Gly Val His Glu Cys Pro Ala Trp Leu Trp Leu Leu Leu Ser Leu
1               5                   10                  15

Leu Ser Leu Val Leu Leu Pro Val Ala Ser
            20                  25
```